US007993393B2

(12) United States Patent
Carpentier et al.

(10) Patent No.: US 7,993,393 B2
(45) Date of Patent: Aug. 9, 2011

(54) FLEXIBLE HEART VALVE AND ASSOCIATED CONNECTING BAND

(75) Inventors: Alain F. Carpentier, Paris (FR); Stefan G. Schreck, Fallbrook, CA (US); Richard S. Rhee, Anaheim Hills, CA (US); Diana Nguyen-Thien-Nhon, Irvine, CA (US); Hung Ly Lam, Norco, CA (US); William J. Recktenwald, Clarence Ctr., NY (US); Robert Frater, Bronxville, NY (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 12/557,404

(22) Filed: Sep. 10, 2009

(65) Prior Publication Data

US 2010/0057193 A1 Mar. 4, 2010

Related U.S. Application Data

(63) Continuation of application No. 12/391,212, filed on Feb. 23, 2009, now abandoned, which is a continuation of application No. 12/188,826, filed on Aug. 8, 2008, now abandoned, which is a continuation of application No. 10/729,035, filed on Dec. 5, 2003, now Pat. No. 7,481,838, which is a continuation of application No. 09/847,930, filed on May 3, 2001, now Pat. No. 6,736,845, which is a continuation-in-part of application No. 09/332,759, filed on Jun. 14, 1999, now Pat. No. 6,558,418.

(60) Provisional application No. 60/117,445, filed on Jan. 26, 1999.

(51) Int. Cl.
*A61F 2/24* (2006.01)
(52) U.S. Cl. ........................................ 623/2.14; 623/2.4
(58) Field of Classification Search .................. 623/2.18
See application file for complete search history.

(56) References Cited

U.S. PATENT DOCUMENTS 3,197,788 A 8/1965 Segger
(Continued)

FOREIGN PATENT DOCUMENTS

EP 0084395 B1 8/1986
(Continued)

OTHER PUBLICATIONS

Japanese Office Action dated Feb. 27, 2008.
(Continued)

*Primary Examiner* — David Isabella
*Assistant Examiner* — Jonathan Stroud
(74) *Attorney, Agent, or Firm* — AnneMarie Kaiser; Guy L. Cumberbatch, Esq.

(57) ABSTRACT

A highly flexible tissue-type heart valve is disclosed having a structural stent in a generally cylindrical configuration with cusps and commissures that are permitted to move radially. The stent commissures are constructed so that the cusps are pivotably or flexibly coupled together at the commissures to permit relative movement therebetween. The stent may be cloth-covered and may be a single element or may be made in three separate elements for a three cusp valve, each element having a cusp portion and two commissure portions; adjacent commissure portions for each pair of adjacent stent element combining to form the stent commissures. If the stent has separate elements their commissure portions may be pivotably or flexible coupled, or may be designed to completely separate into independent leaflets at bioresorbable couples. The cloth covering may have an outwardly projecting flap that mates with valve leaflets (e.g., pericardial leaflets) along the cusps and commissures. A connecting band may be provided that follows the cusps and commissures and extends outwardly. The valve is connected to the natural tissue along the undulating connecting band using conventional techniques, such as sutures. The connecting band may be a cloth-covered silicon member and attaches to the underside of the valve at the cusps to provide support to the stent and to the outer side of the valve at the commissures. The connecting band includes commissure portions defining generally axial gaps that help permit flexing of the valve.

21 Claims, 29 Drawing Sheets

U.S. PATENT DOCUMENTS

| | | | |
|---|---|---|---|
| 3,656,185 | A | 4/1972 | Carpentier |
| 3,714,671 | A | 2/1973 | Edwards et al. |
| 4,055,861 | A | 11/1977 | Carpentier et al. |
| 4,084,268 | A | 4/1978 | Ionescu et al. |
| 4,164,046 | A | 8/1979 | Cooley |
| 4,217,665 | A | 8/1980 | Bex et al. |
| 4,259,753 | A | 4/1981 | Liotta et al. |
| 4,291,420 | A | 9/1981 | Reul |
| 4,297,749 | A | 11/1981 | Davis et al. |
| 4,343,048 | A | 8/1982 | Ross et al. |
| 4,388,735 | A | 6/1983 | Ionescu et al. |
| 4,451,936 | A | 6/1984 | Carpentier et al. |
| 4,470,157 | A | 9/1984 | Love |
| 4,501,030 | A * | 2/1985 | Lane ............ 623/2.18 |
| 4,602,911 | A | 7/1986 | Ahmadi et al. |
| 4,626,255 | A | 12/1986 | Reichart et al. |
| 4,725,274 | A | 2/1988 | Lane et al. |
| 4,778,461 | A | 10/1988 | Pietsch et al. |
| 4,851,000 | A | 7/1989 | Gupta |
| 5,041,130 | A | 8/1991 | Cosgrove et al. |
| 5,061,277 | A | 10/1991 | Carpentier et al. |
| 5,064,431 | A | 11/1991 | Gilbertson et al. |
| 5,104,407 | A | 4/1992 | Lam et al. |
| 5,147,391 | A | 9/1992 | Lane |
| 5,163,953 | A | 11/1992 | Vince |
| 5,163,955 | A | 11/1992 | Love et al. |
| 5,201,880 | A | 4/1993 | Wright et al. |
| 5,258,021 | A | 11/1993 | Duran |
| 5,258,023 | A | 11/1993 | Reger |
| 5,306,296 | A | 4/1994 | Wright et al. |
| 5,411,552 | A | 5/1995 | Andersen et al. |
| 5,449,384 | A | 9/1995 | Johnson |
| 5,489,297 | A | 2/1996 | Duran |
| 5,489,298 | A | 2/1996 | Love et al. |
| 5,496,336 | A | 3/1996 | Cosgrove et al. |
| 5,500,016 | A | 3/1996 | Fisher |
| 5,549,665 | A | 8/1996 | Vesely et al. |
| 5,554,185 | A | 9/1996 | Block et al. |
| 5,593,435 | A | 1/1997 | Carpentier et al. |
| 5,607,471 | A | 3/1997 | Seguin et al. |
| 5,674,279 | A | 10/1997 | Wright et al. |
| 5,697,382 | A | 12/1997 | Love et al. |
| 5,702,368 | A | 12/1997 | Stevens et al. |
| 5,716,417 | A | 2/1998 | Girard et al. |
| 5,728,152 | A | 3/1998 | Mirsch, II et al. |
| 5,776,189 | A | 7/1998 | Khalid |
| 5,800,527 | A | 9/1998 | Jansen et al. |
| 5,824,066 | A | 10/1998 | Gross |
| 5,855,601 | A | 1/1999 | Bessler et al. |
| 5,861,028 | A | 1/1999 | Angell |
| 5,888,240 | A | 3/1999 | Carpentier et al. |
| 5,895,420 | A | 4/1999 | Mirsch, II et al. |
| 5,928,281 | A | 7/1999 | Huynh et al. |
| 5,935,163 | A | 8/1999 | Gabbay |
| 5,964,770 | A | 10/1999 | Flomenblit et al. |
| 5,972,030 | A | 10/1999 | Garrison et al. |
| 6,074,419 | A | 6/2000 | Healy et al. |
| 6,102,845 | A | 8/2000 | Woodard et al. |
| 6,102,945 | A | 8/2000 | Campbell |
| 6,143,024 | A | 11/2000 | Campbell et al. |
| 6,159,240 | A | 12/2000 | Sparer et al. |
| 6,183,512 | B1 | 2/2001 | Howanec, Jr. et al. |
| 6,187,040 | B1 | 2/2001 | Wright |
| 6,217,610 | B1 | 4/2001 | Carpentier et al. |
| 6,231,602 | B1 | 5/2001 | Carpentier et al. |
| 6,250,308 | B1 | 6/2001 | Cox |
| 6,258,122 | B1 | 7/2001 | Tweden et al. |
| 6,332,893 | B1 | 12/2001 | Mortier et al. |
| 6,338,740 | B1 | 1/2002 | Carpentier |
| 6,368,348 | B1 | 4/2002 | Gabbay |
| 6,391,054 | B2 | 5/2002 | Carpentier et al. |
| 6,406,493 | B1 | 6/2002 | Tu et al. |
| 6,419,696 | B1 | 7/2002 | Ortiz et al. |
| 6,558,418 | B2 | 5/2003 | Carpentier et al. |
| 6,602,288 | B1 | 8/2003 | Cosgrove et al. |
| 6,602,289 | B1 | 8/2003 | Colvin et al. |
| 6,619,291 | B2 | 9/2003 | Hlavka et al. |
| 6,689,164 | B1 | 2/2004 | Seguin |
| 6,709,456 | B2 | 3/2004 | Langberg et al. |
| 6,718,985 | B2 | 4/2004 | Hlavka et al. |
| 6,719,786 | B2 | 4/2004 | Ryan et al. |
| 6,726,717 | B2 | 4/2004 | Alfieri et al. |
| 6,764,510 | B2 | 7/2004 | Vidlund et al. |
| 6,797,002 | B2 | 9/2004 | Spence et al. |
| 6,800,090 | B2 | 10/2004 | Alferness et al. |
| 6,802,860 | B2 | 10/2004 | Cosgrove et al. |
| 6,805,710 | B2 | 10/2004 | Bolling et al. |
| 6,805,711 | B2 | 10/2004 | Quijano et al. |
| 6,858,039 | B2 | 2/2005 | McCarthy |
| 6,918,917 | B1 | 7/2005 | Nguyen et al. |
| 6,921,407 | B2 | 7/2005 | Nguyen et al. |
| 6,942,694 | B2 | 9/2005 | Liddicoat et al. |
| 6,955,689 | B2 | 10/2005 | Ryan et al. |
| 6,966,924 | B2 | 11/2005 | Holmberg |
| 6,986,775 | B2 | 1/2006 | Morales et al. |
| 7,101,395 | B2 | 9/2006 | Tremulis et al. |
| 7,118,595 | B2 | 10/2006 | Ryan et al. |
| 7,125,421 | B2 | 10/2006 | Tremulis et al. |
| 7,166,126 | B2 | 1/2007 | Spence et al. |
| 7,166,127 | B2 | 1/2007 | Spence et al. |
| 7,294,148 | B2 | 11/2007 | McCarthy |
| 7,361,190 | B2 | 4/2008 | Shaoulian et al. |
| 7,367,991 | B2 | 5/2008 | McCarthy et al. |
| 7,452,376 | B2 | 11/2008 | Lim |
| 7,608,103 | B2 | 10/2009 | McCarthy |
| 2007/0100441 | A1 | 5/2007 | Kron |
| 2009/0036979 | A1 | 2/2009 | Redmond |
| 2009/0177276 | A1 | 7/2009 | Carpentier |
| 2010/0145440 | A1 | 6/2010 | Keranen |

FOREIGN PATENT DOCUMENTS

| | | |
|---|---|---|
| EP | 0338994 | 10/1989 |
| EP | 0515324 B1 | 12/1996 |
| EP | 1034753 | 9/2000 |
| GB | 2279134 A | 12/1994 |
| SU | 1806696 A1 | 4/1993 |
| WO | WO83/00617 | 3/1983 |
| WO | WO83/02225 | 7/1983 |
| WO | WO90/11738 | 10/1990 |
| WO | WO92/12690 | 8/1992 |
| WO | WO93/18721 | 9/1993 |
| WO | WO95/28899 | 11/1995 |
| WO | WO97/46177 | 12/1997 |
| WO | WO98/43556 | 10/1998 |
| WO | WO00/64382 | 4/1999 |
| WO | WO00/00107 | 1/2000 |
| WO | WO00/042950 | 7/2000 |
| WO | WO00/67661 | 11/2000 |

OTHER PUBLICATIONS

Japanese Patent Publication for Opposition No. 61-9057.

Japanese National Phase PCT Patent Publication No. 7-502918.

Adams, David, et al., "Large Annuloplasty Rings Facilitate Mitral Valve Repair in Barlow's Disease," Society of Thoracic Surgeons 42$^{nd}$ Annual Meeting, Jan. 30-Feb. 1, 2006.

Alonso-Lei, M.D., et al., Adjustable Annuloplasty for Tricuspid Insufficiency, The annals of Thoracic Surgery, vol. 46, No. 3, pp. 368-369, Sep. 1988.

Bernhard, et al "A semi-Supported Porcine Xenograft-Description and First Clinical Use" Thorac Cardiovasc Surgeon 37 (198) pp. 313-315.

Bolling, et al., Surgical Alternatives for Heart Failure, The Journal of Heart and Lung Transplantation, vol. 20, No. 7, pp. 729-733, 2001.

Bolling, Mtral Valve Reconstruction in the Patient With Heart Failure, Heart Failure Reviews, 6, pp. 177-185, 2001.

Carpentier, et al. "The 'Physio-Ring': An Advanced Concept in Mitral Valve Annuloplasty," Society of Thoracic Surgeons 31$^{st}$ Annual meeting, Jan. 30-Feb. 2, 1995.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

D.C. Miller, IMR Redux- To Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Jensen, et al., "New J-3 Flexible-Leaflet Polyurethane Heart Valve Prosthesis with Improved Hydrodynamic Performance." International Journal of Artificial Organ vol. 14.10, 1991/pp. 655-660.

Krucinski, et al., "Numerical Stimulation of Leaflet Flexure in Bioprosthetic Valves Mounted on Rigid and Expansible Stents." J. Biomechanics, vol. 2/No. 8, 1993/ pp. 29-943.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Salgo, et al., Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association © 2005; ISSN: 1524-4539.

* cited by examiner

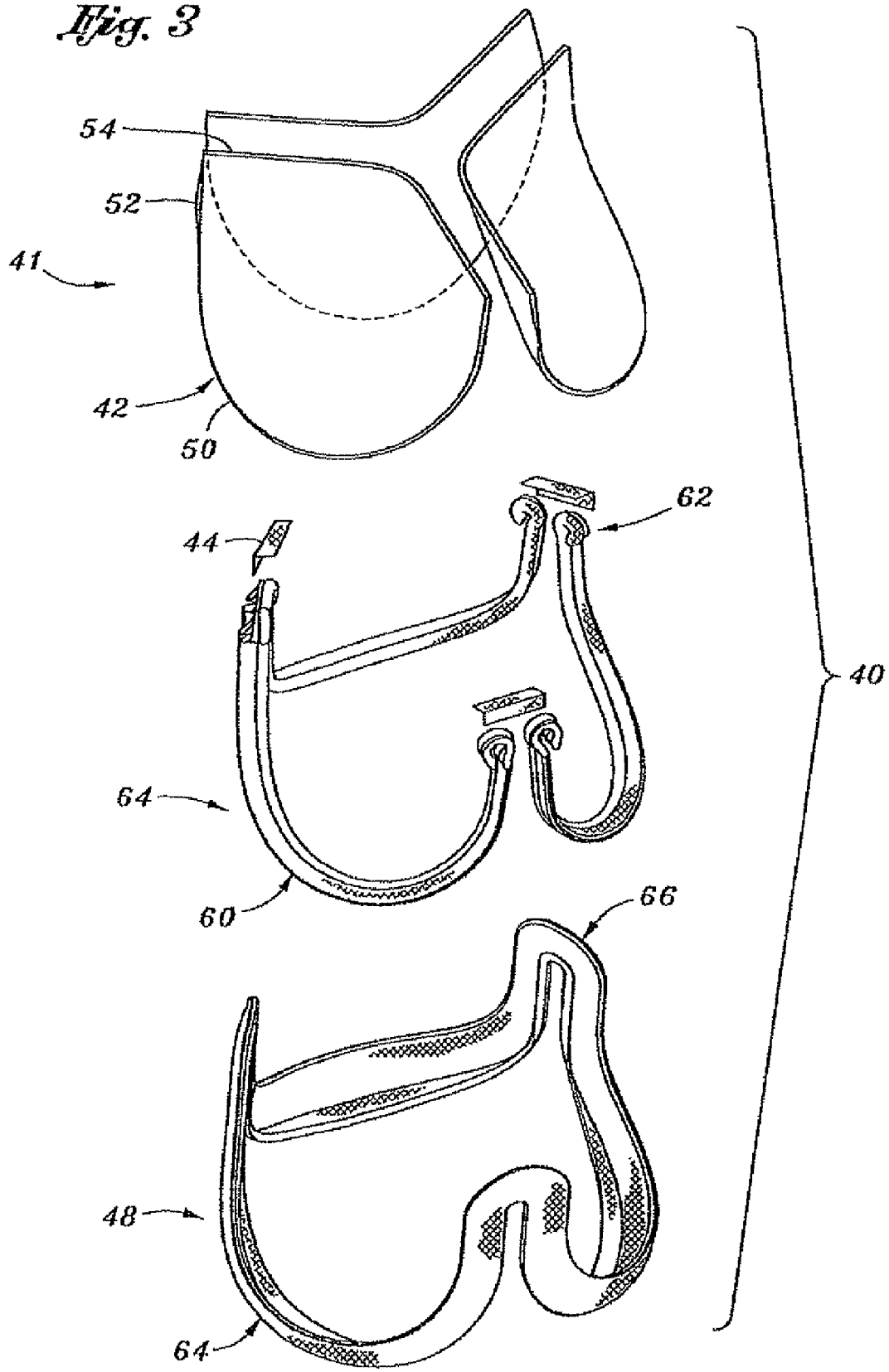

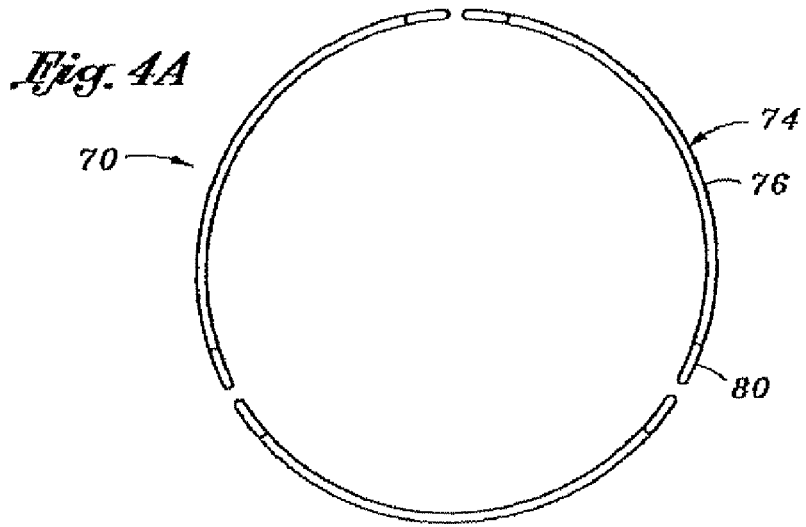
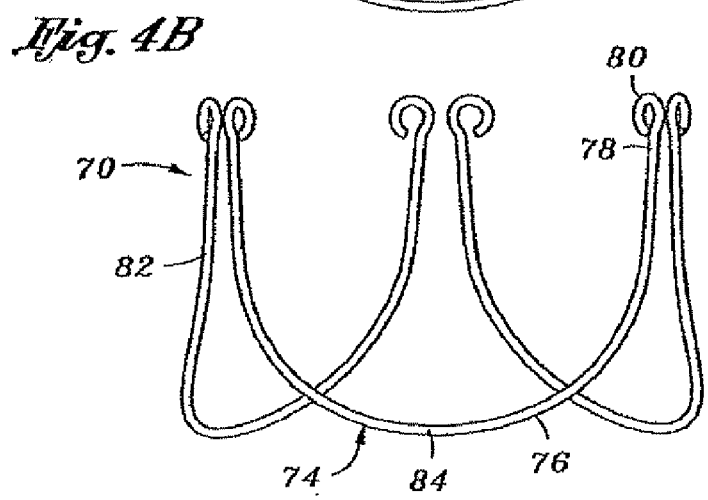
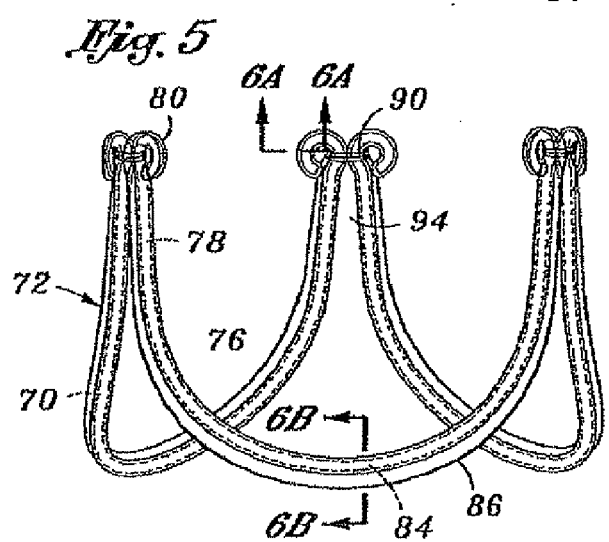
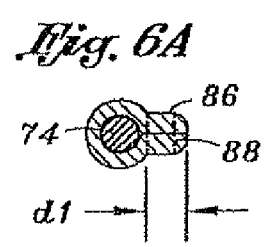
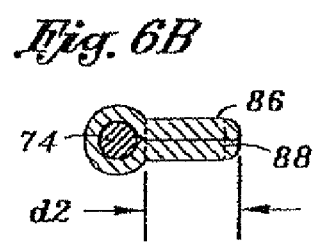

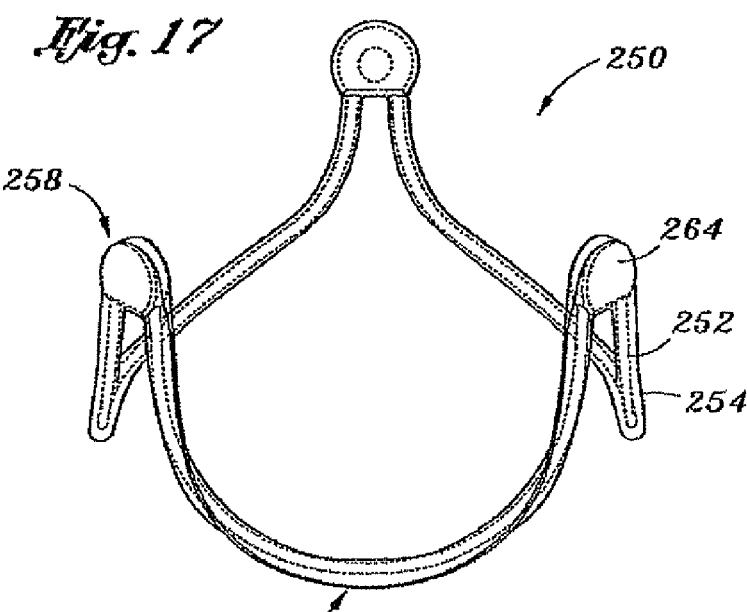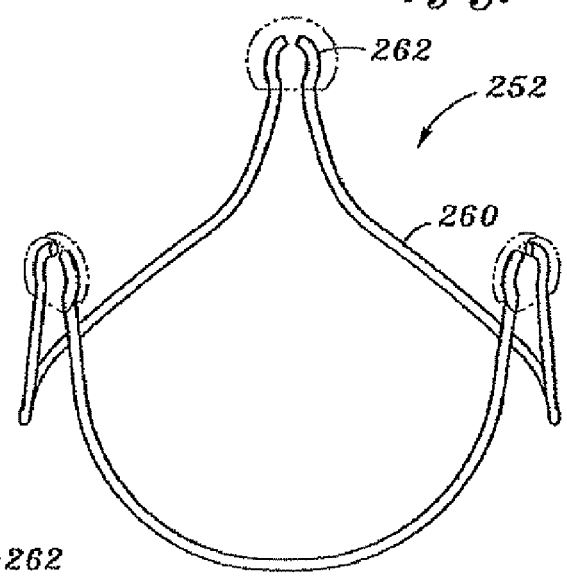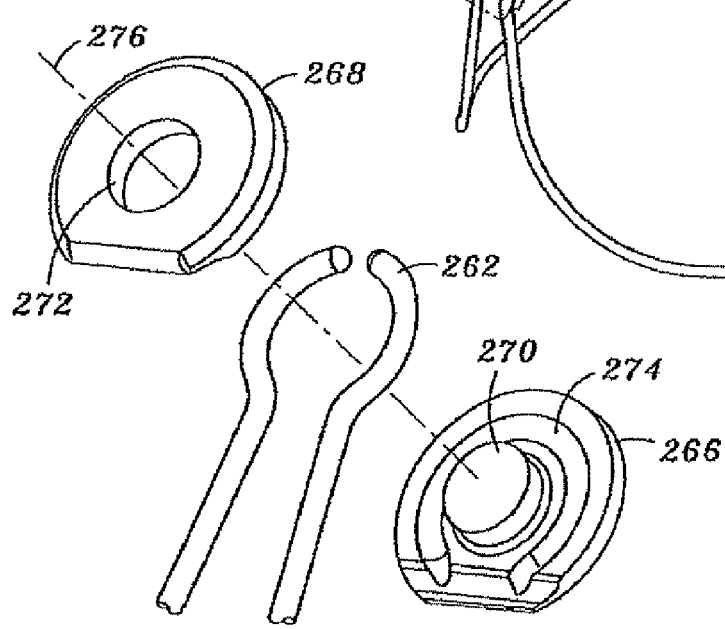

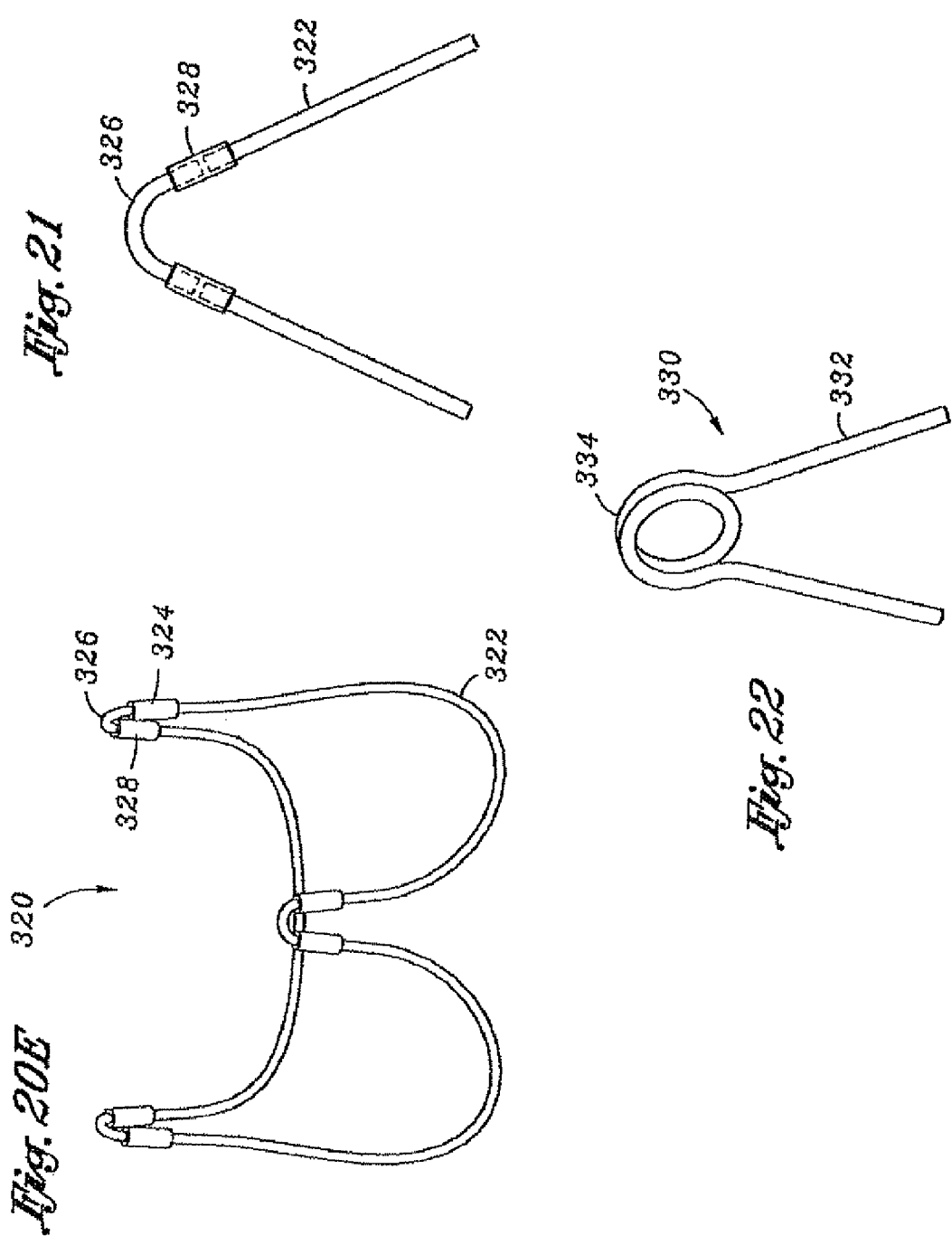

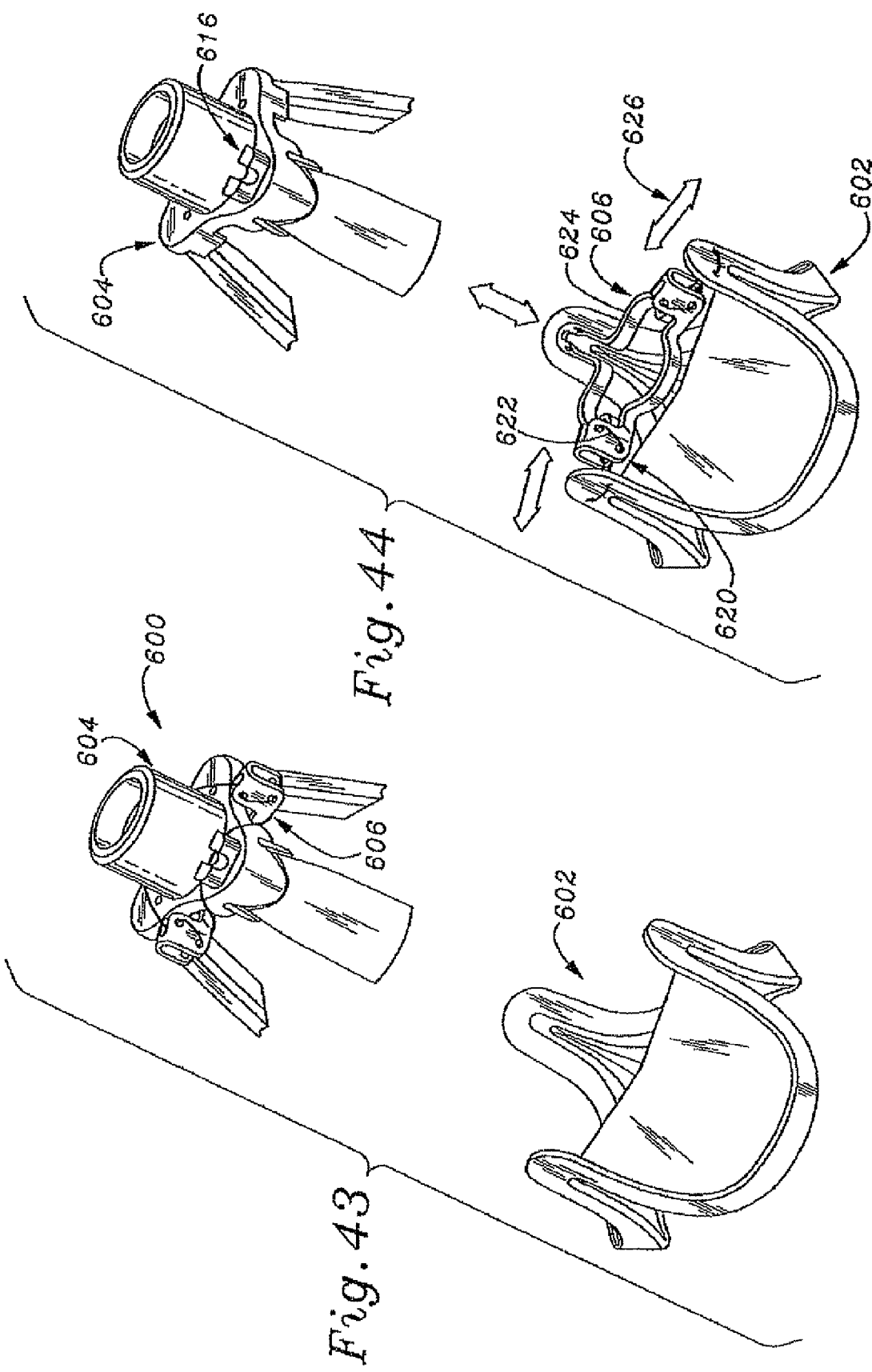

US 7,993,393 B2

FLEXIBLE HEART VALVE AND ASSOCIATED CONNECTING BAND

RELATED APPLICATIONS

The present application is a continuation of U.S. application Ser. No. 12/391,212 filed Feb. 23, 2009, now abandoned, which is a continuation of U.S. application Ser. No. 12/188,826 filed Aug. 8, 2008, now abandoned, which is a continuation of U.S. application Ser. No. 10/729,035, filed Dec. 5, 2003, now U.S. Pat. No. 7,481,838, which is a continuation of U.S. application Ser. No. 09/847,930, filed May 3, 2001, now U.S. Pat. No. 6,736,845, which is a continuation-in-part of U.S. application Ser. No. 09/332,759, filed Jun. 14, 1999, now U.S. Pat. No. 6,558,418, which claims priority under 35 U.S.C §119(e) to provisional application No. 60/117,445, filed on Jan. 26, 1999, the disclosures of which are expressly incorporated herein by reference.

FIELD OF THE INVENTION

The present invention relates to prosthetic heart valves, and, more particularly, to a highly flexible prosthetic tissue valve and associated connecting band or sewing ring.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way outflow valve. The natural heart valves are identified as the aortic, mitral (or bicuspid), tricuspid and pulmonary valves. The valves of the heart separate chambers therein, and are each mounted in an annulus therebetween. The annuluses comprise dense fibrous rings attached either directly or indirectly to the atrial and ventricular muscle fibers. Prosthetic heart valves can be used to replace any of these naturally occurring valves, although repair or replacement of the aortic or mitral valves are most common because they reside in the left side of the heart where pressures are the greatest. In a valve replacement operation, the damaged leaflets are excised and the annulus sculpted to receive a replacement valve.

The four valves separate each ventricle from its associated atrium, or from the ascending aorta (left ventricle) or pulmonary artery (right ventricle). After the valve excision, the annulus generally comprises a ledge extending into and defining the orifice between the respective chambers. Prosthetic valves may attach on the upstream or downstream sides of the annulus ledge, but outside of the ventricles to avoid interfering with the large contractions therein. Thus, for example, in the left ventricle a prosthetic valve is positioned on the inflow side of the mitral valve annulus (in the left atrium), or on the outflow side of the aortic valve annulus (in the ascending aorta).

Two primary types of heart valve replacements or prostheses are known. One is a mechanical-type heart valve that uses a ball and cage arrangement or a pivoting mechanical closure to provide unidirectional blood flow. The other is a tissue-type or "bioprosthetic" valve which is constructed with natural-tissue valve leaflets which function much like a natural human heart valve, imitating the natural action of the flexible heart valve leaflets which seal against each other to ensure the one-way blood flow.

Prosthetic tissue valves comprise a stent having a rigid, annular ring portion and a plurality of upstanding commissures to which an intact xenograft valve or separate leaflets of, for example, bovine pericardium are attached. The entire stent structure is typically cloth-covered and a sewing ring is provided around the periphery for attaching to the natural annulus. Because of the rigidity of the material used in the stent and/or wireform, conventional valves have a diameter that is minimally affected by the natural motion of the heart orifice. In the aortic position, the commissures extend in the downstream direction a spaced distance from the walls of the downstream aortic wall. Movement of the aortic wall or sinuses does not directly affect movement of the cantilevered commissures, though fluid flow and pressures generated by movement of the walls ultimately does cause the commissures to dynamically flex to some extent (i.e., they are cantilevered downstream in the aorta). Because of the inherent rigidity in conventional heart valves, the natural dilatation of the annulus is restricted, imposing an artificial narrowing of the orifice, and increasing the pressure drop therethrough.

Accordingly, there is a need for a more flexible heart valve that responds to the natural motions of the annulus and downstream vessel walls.

SUMMARY OF THE INVENTION

The present invention allows the prosthesis to follow the aortic wall motion as well as that of the annulus during systole and diastole phases, thus reducing the loss in pressure caused by restriction of such motions. The solution is a heart valve having a plurality of leaflets, preferably three, directly sutured to the aortic wall, replacing the native valve.

The present invention provides a heart valve including a flexible wireform or stent that allows relative cusp movement or pivoting. The continuous maintenance of leaflet orientation at the commissures provides durability and predictability. Though the leaflets are not wholly independent, they are allowed to move in regions of greatest anatomical motion.

The present invention differs in another respect from bioprosthetic tissue valves of the prior art because it does not include a conventional sewing ring with attendant rigid stent. Alternating peripheral cusps and commissures of the prosthetic valve are attached to the annulus region and the sinus region of the ascending aorta of the host (in the aortic valve version), downstream from the location of the natural leaflets (typically excised).

In accordance with one aspect of the present invention, a prosthetic heart valve is provided including a flexible, generally cylindrical stent having alternating cusps and commissures. A plurality of flexible leaflets is attached to the stent so as to form a one-way valve within the cylinder. A flexible band is attached along the stent and has a free edge extending away from the stent along the alternating cusps and commissures for connecting the heart valve to an anatomical orifice.

Another aspect of the present invention is a highly flexible heart valve including a stent/leaflet subassembly having a peripheral stent and a plurality of leaflets disposed therewithin. The stent/leaflet subassembly defines alternating cusps and the commissures. A connecting band is attached to the stent/leaflet subassembly and follows the alternating cusps and commissures. The band includes a free edge extending from the stent for connecting the heart valve to an anatomical orifice.

In a still further aspect of present invention, a prosthetic heart valve comprises a plurality of flexible leaflets, each having an arcuate cusp edge and a coapting edge. The heart valve includes a stent with a plurality of cusps connected to each other at upstanding commissures to generally define a substantially cylindrical volume therebetween. The leaflets are attached to the stent within the cylindrical volume and the cusps are free to move with respect to one another about the commissures.

In another embodiment, the present invention provides a prosthetic heart valve comprising a stent having a plurality of stent members adjacently disposed generally around a circle to define a substantially cylindrical volume therebetween. The stent includes a plurality of alternating cusps and commissures. Preferably, the stent members each have a cusp and two commissure regions, with adjacent commissure regions of the stent members together defining each of the commissures of the stent. The stent members may be coupled together to pivot or flexibly move with respect to one another. The coupling may be permanent, or may comprise a bio-resorbable structure that permits the stent members and associated leaflets to move independently from one another.

Desirably, the stent of the prosthetic heart valve of the present invention is configured to permit the cusps and commissures to move radially in and out. In one embodiment, the stent comprises a cloth covered rod-like structure. The cloth covering closely surrounds the stent and includes a flap projecting therefrom substantially the entire length of the cusps and commissures for connecting the stent to both the flexible band and the leaflets. The band preferably comprises a suture-permeable inner member, such as silicone, covered by cloth. The cusps of the stent may be pivotally or flexibly coupled to each other at the commissures. Preferably, the stent comprises separate cloth-covered stent members that each define a cusp region and two commissure regions, adjacent commissure regions of the stent members together defining each of the commissures of the stent. The commissure regions of the separate stent members desirably remain spaced apart, with the leaflets extending therethrough to be attached between the cloth covering and the outer connecting band. In this manner, the leaflets are connected to separate stent members, and not to each other to facilitate flexing of the valve.

In another aspect of the present invention, a holder is provided for mounting the flexible heart valve. The holder includes a central hub with a plurality of radially outward upper legs, and a plurality of lower legs angled downward and outward. The upper and lower legs are adapted to connect to the alternating cusps and commissures of a flexible valve so as to maintain the position of the valve during implantation.

The present invention further provides a combination of a flexible prosthetic heart valve and a rigid holder. The flexible heart valve includes alternating cusps and commissures in a generally cylindrical configuration adapted to move radially in and out with respect to one another. The holder includes structure for maintaining a fixed shape of the flexible prosthetic heart valve during implantation.

In a still further aspect of the present invention, a heart valve leaflet is provided comprising a flexible, planar body having an arcuate cusp edge terminating at outer tips. The planar body includes a coapting edge that is defined by two relatively angled lines joined at an apex directed away from the cusp edge midway between the two tips. Desirably, the leaflet is made of pericardial tissue.

The present invention further provides a method of implantation of a heart valve, including the steps of: providing a flexible heart valve having alternating cusps and commissures in a generally cylindrical configuration and adapted to move radially in out with respect to one another; attaching a holder to the valve that restricts relative movement of the cusps and commissures; positioning the heart valve in proximity to an anatomical orifice; implanting the heart valve; and, disconnecting the holder from heart valve.

The present invention provides a holder for a heart valve including a flexible stent that allows relative cusp movement or pivoting. The continuous maintenance of leaflet orientation at the commissures provides durability and predictability. Though the leaflets are not wholly independent, they are allowed to move in regions of greatest anatomical motion. The heart valve may be highly flexible and include a stent/leaflet subassembly having a peripheral stent and a plurality of leaflets disposed therewithin. The stent/leaflet subassembly defines alternating cusps and the commissures. A connecting band may be attached to the stent/leaflet subassembly and follows the alternating cusps and commissures. The band may include a free edge extending from the stent for connecting the heart valve to an anatomical orifice.

In one aspect of the invention, a holder for attaching to and holding a flexible heart valve is provided. The heart valve is of the type that has multiple leaflets joined together at a periphery of the valve at valve commissures that are generally axially aligned and evenly disposed about a valve axis, the valve commissures are located between adjacent curvilinear valve cusps along the periphery of the valve. The holder comprises a plurality of cusp supports arranged around an axis to contact the heart valve generally along the valve cusps, and a plurality of commissure supports connected to and intermediate each two cusp supports and arranged to abut the valve commissures. The commissure supports are desirably radially flexible enabling the valve commissures to be flexed inward while in contact with the holder commissure supports. For example, the commissure supports may be made of Nitinol. Preferably, at least one leg extends radially inward from a cusp support to a location surrounded by the plurality of cusp supports, and more preferably multiple legs extend radially inward from each cusp support and attach together at a common location. The common location may be on the axis of the holder that coincides with the valve axis when the holder and valve are attached.

A connector may be provided extending along the holder axis to which the legs join. The connector has a coupling for receiving a handle for the holder and a length suitable for manually grasping. In one embodiment, the connector is formed separately from the legs and joined thereto. In addition, the legs may be formed separately from the cusp supports and joined thereto.

In an exemplary form, the cusp supports are multiple pieces joined together, wherein each piece may include two halves of adjacent cusp supports and a commissure support. In the multiple piece embodiment, multiple legs may extend radially inward from each cusp support and attach together at a common location, wherein each piece has two leg halves extending radially inward from each of its cusp support halves, and wherein each pair of adjacent leg halves makes up one of the holder legs.

The holder may further include a central hub with a plurality of radially outward upper legs connected to the commissure supports, and a plurality of lower legs angled downward and outward connected to the cusp supports. Each lower leg preferably has a width from the hub to a terminal end that is greatest at the terminal end to provide more surface area to contact the corresponding valve cusp.

Another aspect of the invention is a combined flexible heart valve and holder. The combination includes a prosthetic flexible heart valve having multiple leaflets joined together at a periphery of the valve at valve commissures that are generally axially aligned and evenly disposed about a valve axis. The valve commissures are configured for radial movement with respect to the valve axis and are each disposed between adjacent curvilinear valve cusps along the periphery of the valve.

The valve leaflets coapt along the valve axis and curve in a direction to form an inflow side and an outflow side of the valve. The combination includes a holder attached to the outflow side of the valve having cusp supports that contact and axially support the valve cusps. The holder also has commissure supports between each two of the cusp supports that axially support the valve commissures yet permit radial their radial movement with respect to the valve axis.

The holder preferably includes structure for substantially preventing torsional deformation of the flexible heart valve during implantation. The holder further may include a valve contacting portion having a generally continuous curvilinear structure conforming to the periphery of the valve and defining the alternating cusp and commissure supports. A central hub with a plurality of legs angled downward and outward may be connected to the cusp supports. In one version, the valve contacting portion is integrally formed separate from the legs, while in another the valve contacting portion is formed of a plurality of separate pieces, each piece defining at least a part of one of the legs. Each separate piece may define a half of two adjacent cusp supports, and may be formed of a wire.

The combination further may include commissure attachment sutures connecting the commissure supports to the valve commissures. The flexible heart valve may include a sewing band that generally conforms to the valve cusps and commissures, wherein the commissure attachment sutures connect the commissure supports to the sewing band at the valve commissures. The holder further may include a valve contacting portion having a generally continuous curvilinear structure conforming to the periphery of the valve and defining the alternating cusp and commissure supports, wherein the commissure attachment sutures are severable at the commissure supports and wherein the commissure supports include leaflet guard sections that structurally protect the valve leaflets from being cut by a blade in severing the commissure attachment sutures.

The combination further may include cusp attachment sutures connecting the cusp supports to the valve cusps. The flexible heart valve may include a sewing band that generally conforms to the valve cusps and commissures, wherein the cusp attachment sutures connect the cusp supports to the sewing band at the valve cusps. Desirably the cusp attachment sutures are routed so as to cross a common cut point on the holder such that the plurality of attachments between the cusp supports and valve cusps can be severed with one cut. The holder may further include a central hub with a plurality of legs angled downward and outward connected to the cusp supports, wherein the cusp attachment sutures each loop through the valve at the valve cusps with one segment being tied to the cusp support and a second segment extending up the corresponding leg to the hub, across the common cut point. A sleeve may surround each leg within which the second segment is contained.

The holder may include two stages, a first stage having the cusp supports and a second stage having the commissure supports, the two stages being formed so as to be separable. The first stage may include a central hub and a plurality of legs angling outward and downward to form the cusp supports at their terminal ends. The second stage may include a flexible band around which the commissure supports are spaced, the band permitting the commissure supports to flex radially with respect to one another.

In another aspect of the present invention, a holder is provided for mounting the flexible heart valve. The holder includes a central hub with a plurality of radially outward upper legs, and a plurality of lower legs angled downward and outward. The upper and lower legs are adapted to connect to the alternating cusps and commissures of a flexible valve so as to maintain the position of the valve during implantation.

The present invention further provides a combination of a flexible prosthetic heart valve and a rigid holder. The flexible heart valve includes alternating cusps and commissures in a generally cylindrical configuration adapted to move radially in and out with respect to one another. The holder includes structure for maintaining a relatively fixed shape of the flexible prosthetic heart valve during implantation.

The present invention further provides a method of implantation of a heart valve, including the steps of: providing a flexible heart valve having alternating cusps and commissures in a generally cylindrical configuration and adapted to move radially in out with respect to one another; attaching a holder to the valve that restricts relative axial and torsional movement of the cusps and commissures; positioning the heart valve in proximity to an anatomical orifice; implanting the heart valve; and, disconnecting the holder from heart valve. The holder may include cusp supports that contact and axially support the valve cusps and commissure supports between each two of the cusp supports that axially support the valve commissures yet permit radial their radial movement with respect to the valve axis. In the latter case, the method may include visualizing the site of valve implantation by flexing one of the valve commissures radially inward while being supported by the corresponding commissure support of the holder.

BRIEF DESCRIPTION OF THE DRAWINGS

FIG. 3 is an exploded perspective view illustrating sub-assemblies of a prosthetic heart valve of the present invention;

FIG. 4A is a top plan view of an internal stent of the prosthetic heart valve of the present invention;

FIG. 4B is an elevational view of the internal stent of FIG. 4A;

FIG. 5 is an elevational view of a stent assembly of the prosthetic heart valve;

FIGS. 6A and 6B are sectional views through two locations of the stent assembly, taken along lines 6A-6A and 6B-6B of FIG. 5;

FIG. 17 is a perspective view of an alternative stent assembly for use in a prosthetic heart valve in accordance with the present invention;

FIG. 18 is a perspective view of an internal stent of the stent assembly of FIG. 17;

FIG. 19 is an exploded view of a commissure tip region of the stent assembly of FIG. 17;

FIGS. 20A-20E are elevational views of alternative stents for use in a prosthetic heart valve in accordance with the present invention;

FIG. 21 is a detailed view of a commissure region of the alternative stent of FIG. 20E;

FIG. 22 is a detailed view of a commissure region of a still further alternative stent accordance with the present invention;

FIG. 43 is a perspective view showing the two-stage heart valve holder of FIG. 41 exploded from the flexible heart valve; and FIG. 44 is a perspective view showing the two-stage heart valve holder of FIG. 41 exploded into its two parts with a flexible stage remaining attached to the flexible heart valve.

DESCRIPTION OF THE PREFERRED EMBODIMENTS

The present invention provides a highly flexible aortic heart valve that is attached generally along a scalloped or undulating perimeter downstream from where the natural leaflets were originally attached. The natural leaflets include arcuate cusp portions separated by common commissure portions. If the natural valve has three leaflets, and has a vertically oriented flow axis, the leaflets are evenly distributed circumferentially 120° apart with lower cusp portions and upstanding commissure portions. The commissure portions are connected between the cusp portions and are generally axially aligned along the aortic wall. The annular root of an aortic valve is composed of fibrous tissue and generally conforms to the undulating perimeter of the valve to support the leaflets. In this respect, implanting the aortic heart valve of the present invention involves excising the natural leaflets and attaching the prosthetic heart valve proximate the fibrous annulus, but also in part up the aortic wall. Because of the particular construction of the present heart valve, as will be described below, the attachment means, be it sutures, staples, adhesives, or otherwise, may be anchored into the aortic wall itself, adjacent to the fibrous annulus.

Anatomy

Figure 1:
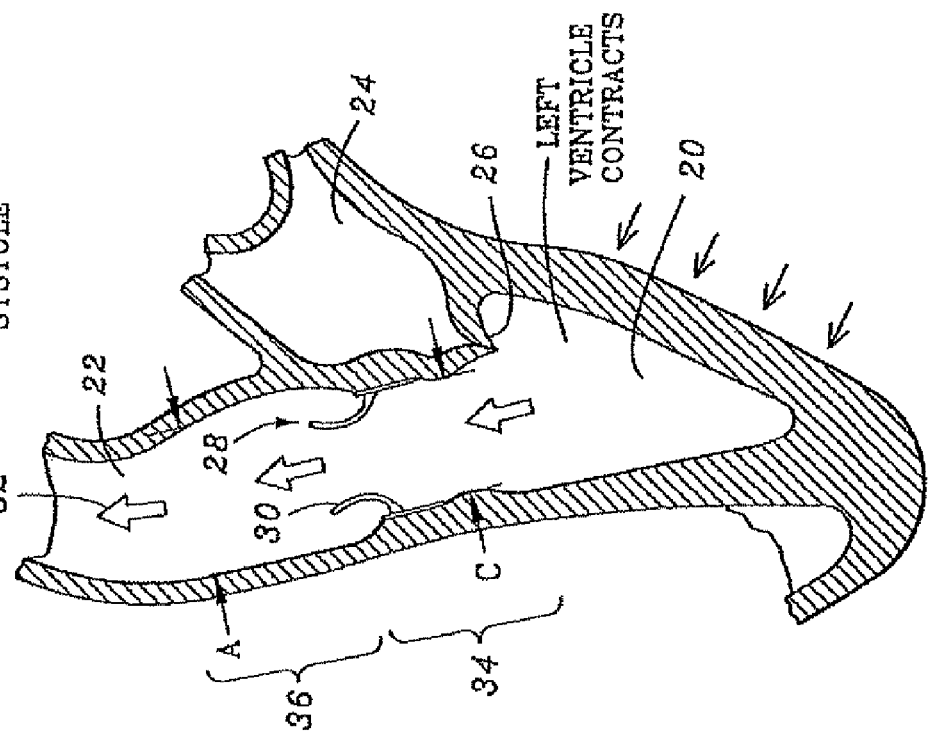
FIG. 1 is a sectional view through the left half of a human heart showing a systolic phase of left ventricular contraction.
Figure 2:
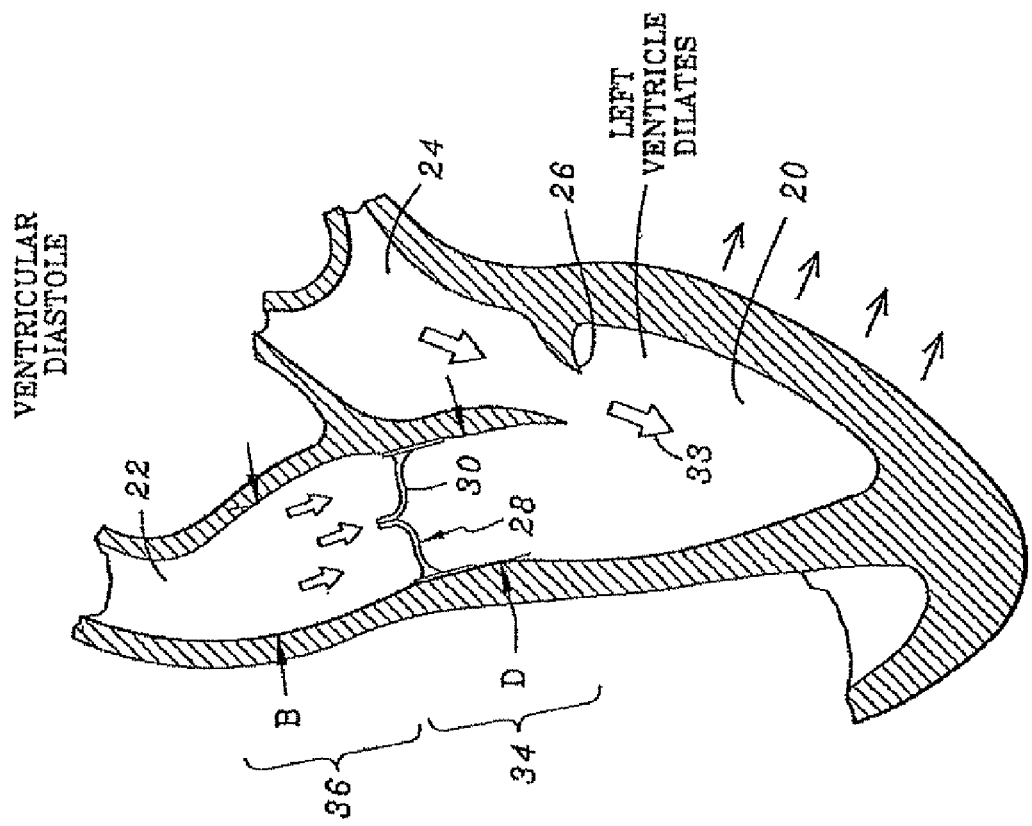
FIG. 2 is a sectional view through the left half of a human heart showing a diastolic phase of left ventricular expansion.

To better illustrate the advantages of the flexible heart valve of the present invention, an understanding of the movement of the annulus and aorta is helpful. In this regard, FIGS. 1 and 2 illustrate the two phases of left ventricular function; systole and diastole. Systole refers to the pumping phase of the left ventricle, while diastole refers to the resting or filling phase. FIGS. 1 and 2 illustrate in cross section the left chamber of the heart with the left ventricle 20 at the bottom, and the ascending aorta 22 and left atrium 24 diverging upward from the ventricle to the left and right, respectively.

FIG. 1 illustrates systole with the left ventricle 20 contracting, while FIG. 2 illustrates diastole with the left ventricle dilating. The aortic valve 28 is schematically illustrated here as having leaflets 30. Contraction of the ventricle 20 causes the mitral valve 26 to close and the aortic valve 28 to open, and ejects blood through the ascending aorta 22 to the body's circulatory system, as indicated in FIG. 1 by the arrows 32. Dilation of the ventricle 20 causes the aortic valves 28 to close and mitral valve 26 to open, and draws blood into the ventricle from the left atrium 24, as indicated in FIG. 2 by the arrows 33.

The walls of the left chamber of the heart around the aortic valve can be generally termed the annulus region 34 and the sinus region 36. The annulus region 34 generally defines an orifice that is the narrowest portion between the ventricle 20 and ascending aorta 22, which as noted above is composed of generally fibrous tissue. The sinus region 36 is that area just downstream from the annulus region 34 and includes somewhat elastic, less fibrous tissue. Specifically, the sinus region 36 typically includes three identifiable, generally concave sinuses (formally known as Sinuses of Valsalva) in the aortic wall intermediate the upstanding commissures of the valve 28. The sinuses are relatively elastic and are constrained by the intermediate, more fibrous commissures of the aortic annulus. Those of skill in the art will understand that the annulus region 34 and sinus region 36 are not discretely separated into either fibrous or elastic tissue, as the fibrous commissures of the annulus extend into the sinus region 36.

The sinuses tend to move in and out to facilitate fluid dynamics of the blood in conjunction with systole and diastole. During systole, as seen in FIG. 1, the sinus region 36 expands somewhat to a diameter A. This facilitates blood flow through the ascending aorta 22 to the rest of the body. In contrast, during the diastolic phase as seen in FIG. 2, the sinus region 36 contracts somewhat to a smaller diameter B. The diameters A and B are intended to be a measurement of the radial movement of the commissure regions of the valve 28. In this regard it will be understood that the cross-sections shown are not taken in a single plane, but instead are taken along two planes angled apart 120° with respect one another and meeting at the midpoint of the aorta 22. The sinus region 36 has a neutral, or relaxed diameter (not shown) somewhere in between diameters A and B.

The annular region 34 also moves in and out during the systolic and diastolic phases. As seen in FIG. 1, the annular region 34 contracts somewhat to a diameter C during systole. In contrast, during the diastolic phase as seen in FIG. 2, the annular region 34 expands somewhat to a larger diameter D. Much like the sinus region 36, the annular region 34 has a neutral, or relaxed diameter (not shown) somewhere in between diameters C and D.

As will be explained more fully below, the prosthetic valve of the present invention accommodates the in and out movements of both the annular region 34 and the sinus region 36. That is, alternating peripheral portions of the prosthetic valve are attached to the annular region 34 and the sinus region 36 and move accordingly. It is important to point out that the preceding discussion of dynamic movement of the annulus and sinus regions is based on preliminary understanding of such movement. That is, direct measurements of these movements are problematic, and thus certain assumptions and predictions must be made. The actual dynamic movement in any particular human heart may be different, but the principles of the present invention would still apply. That is, relative movement in the annulus and sinus regions during systole and diastole does exist, and the flexible prosthetic heart valve of the present invention can accommodate any such movement.

Valve Subassemblies

Figure 11:
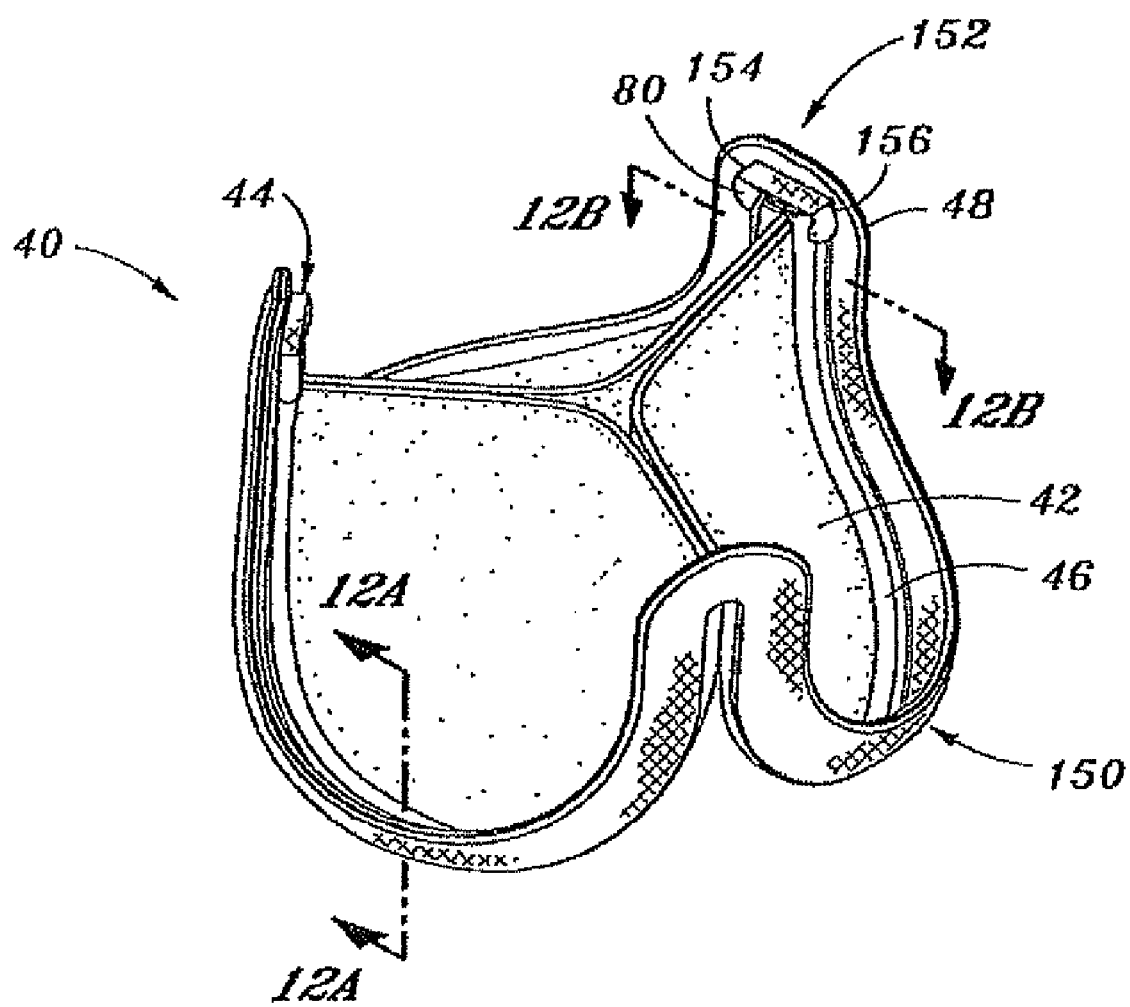
FIG. 11 is a perspective view of an assembled prosthetic heart valve of the present invention.

With reference now to FIG. 3, the primary sub-assemblies of a preferred embodiment of the prosthetic heart valve 40 of the present invention are shown in exploded view. For purposes of discussion, the directions up and down, upper and lower, or top and bottom, are used with reference to FIG. 3, but of course the valve can be oriented in any direction both prior to and after implantation. From top to bottom, the heart valve 40 comprises a group 41 of three leaflets 42, three angled alignment brackets 44, a stent assembly 46, and a connecting band 48. Each of the sub-assemblies seen in FIG. 3 is procured and assembled separately (except for the group of leaflets, as will be explained), and then joined with the other sub-assemblies to form the fully assembled valve 40 as seen in FIG. 11.

The prosthetic valve 40 is a trifoliate valve with three leaflets 42. Although three leaflets are preferred, and mimic the natural aortic valve, the principles of the present invention can be applied to the construction of a prosthetic valve with two or more leaflets, depending on the need.

Each of the sub-assemblies seen in FIG. 3 include three cusps separated by three commissures. The leaflets 42 each include an arcuate lower cusp edge 50 terminating in upstanding commissure regions 52. Each leaflet 42 includes a coapting or free edge 54 opposite the cusp edge 50. In the assembled valve 40, the cusp edges 50 and commissure regions 52 are secured around the periphery of the valve, with the free edges 54 permitted to meet or "coapt" in the middle. The stent assembly 46 also includes three cusps 60 separated by three upstanding commissures 62. In like manner, the connecting band 48 includes three cusp portions 64 separated by three upstanding commissure portions 66. Each of the sub-assemblies will now be described in detail.

Stent Assembly

Various components of a preferred stent assembly 46 are seen in FIGS. 4-6. The stent assembly 46 comprises an inner stent 70 and an outer cloth cover 72. More specifically, the inner stent 70 desirably includes three identical and separate stent members 74, each of which has a separate cloth covering. As seen best in FIG. 4B, each stent member 74 comprises an arcuate lower cusp region 76 and upstanding commissure regions 78 each terminating at a tip 80. The stent members 74 comprise elongate rods or wires, preferably made out of an elastic biocompatible metal and/or plastic alloy, such as Elgiloy®, Nitinol, polypropylene, etc. The material selected for stent members 74 should be elastic to permit flexing along their lengths, but should possess a relatively high modulus of elasticity to avoid asymmetric deformation of the constructed valve 40. The stent 70 supplies an inner frame for the valve 40 that is relatively more rigid than the other components. Therefore, the stent 70 acts to limit total flexibility of the valve 40.

Alternatively, the material for the stent 70 may be highly flexible so as to add relatively little reinforcement to the valve 40. For example, the stent members 74 may be formed of a length of medical grade silicone that provides some physical structure around the valve that helps in stitching fabric around the valve, and also helps provide some bulk for grasping and sewing the valve in place, but otherwise does not reduce the flexibility of the other components. In this case, the stent 70 is desirably formed of a single piece (such as seen in FIG. 20D) and the commissures are inherently flexible, enabling the cusp regions 76 to flex or pivot with respect to one another. This very high flexibility of the valve 40 minimizes any unwanted impediment to the natural annulus and aortic wall movement, and desirably maximizes the flow orifice formed though the valve, thus reducing any pressure loss therethrough. The highly flexible stent material may be provided in one or multiple filaments, with or without a surrounding enclosing sleeve, and may be silicone as mentioned, polypropylene, Delrin, polyurethane, polytetrafluoroethylene (PTFE), or the like. An exemplary thickness of the highly flexible stent material is about 0.011-0.013 inches for a monofilament version, or up to 0.025 inches with multiple filaments.

The stent members 74 are desirably bent into the illustrated shape, using conventional wire-forming techniques. Each of the stent members 74 is identical, and terminates in the tips 80 which are bent inward with respect to the arcuate cusp regions 76 to nearly form closed circles. As is seen in FIG. 4B, a gradual radially outward bend 82 (with respect to the cylindrical stent 70) is provided in the stent members 74 at a transition between each of the commissure regions 78 and the intermediate cusp region 76. This bend 82 permits each of the stent members 74 to remain in a circular configuration, as seen from above in FIG. 4A. That is, if the cusp regions 76 extended in a plane between each of the commissure regions 78, the plan view would be somewhat triangular. Instead, each of the cusp regions 76 includes a lower apex 84, and the apices of all of the cusps define a circle concentric with and having the same diameter as a circle defined by all of the tips 80. The stent 70 thus defines a substantially cylindrical volume therewithin. Of course, other volumes may be defined by the stent 70 wherein the tips 80 define a circle that is smaller or larger than a circle defined by the apices 84. For example, the apices 84 may be provided outward from the tips 80 so the stent 70 defines a frusto-conical volume therewithin.

As seen in FIG. 5, each of the stent members 74 is preferably covered with a generally tubular cloth 72 from tip to tip 80. The cloth cover 72 is a biocompatible fabric, such as polyterephthalate, and has a varying cross sectional shape, as indicated in FIGS. 6A and 6B. More specifically, the cloth cover 72 includes a tubular portion closely conforming around each of the stent members 74 and a flap 86 extending radially outward from the stent member (with respect to the curvature of the cusp regions 76). The cloth cover 72 is formed by wrapping an elongated sheet of fabric around each of the stent members 74 and joining the free edges with sutures 88 to form the flaps 86. As seen in FIG. 5, the flap 86 extends from each stent member 74 in a direction that is generally outward with respect to the cusp region 76, and continues in the same general orientation up the commissure regions 78 to the tips 80. The flap 86 has a dimension that is longest at the apex 84 of each cusp region 76 and shortest at the tips 80. Indeed, the flap 86 is preferably nonexistent at the tips 80, and gradually increases in size from the tip 80 to the apex 84. Therefore, the cross-section of FIG. 6A taken through the commissure region 78 shows the flap 86 having a small dimension d1, and the cross-section of FIG. 6B taken through the apex 84 shows the flap 86 having a longer dimension d2.

The final component of the stent assembly 46 is an attachment means 90 for joining each of a cloth-covered stent members 74. Preferably, the attachment means 90 comprises threads or sutures sewn through the central holes in each of the circular tips 80, as shown in FIG. 5, although other suitable attachment means could be used, such as rings, cinches, or the like. The attachment means 90 may be wrapped around or sewn through the cloth cover 72. In joining the tips 80, the attachment means 90 are desirably not wrapped extremely tightly, but are instead provided with some slack to permit relative movement of the tips, as will be described below. When the stent members 74 are attached, as seen in FIG. 5, the stent 70 exhibits three cusps corresponding to the cusp region 76 of each member, and three upstanding commissures defined by the juxtaposition of adjacent pairs of commissure regions 78.

In a preferred embodiment of the present invention the attachment means 90 comprises a non-bioresorbable material to ensure that the individual stent members 74 are maintained in the shape of the stent 70. In an alternative configuration, however, the attachment means 90 comprises a bioresorbable material that dissolves over a period of time after implantation. In such an embodiment, the natural host tissues may have grown in and around the porous portions of the valve 40 to help retain the original shape of the stent 70. In some instance, however, very little tissue overgrowth may have occurred prior to the attachment means 90 dissolving, and the individual stent members 74 are permitted to move radially a great deal with respect to one another. In the latter embodiment, wherein the stent members 74 are permitted to spread apart, the connecting band 48 may be re-configured to be non-continuous at the commissure portions 66 (see FIG. 3). As a consequence, each individual stent member 74 and associated leaflet 72 moves entirely independently of the others, albeit all oscillating with the natural contractions and expansions of the surrounding aortic wall. Such independent leaflet movement may greatly reduce any potential pressure drop across the valve. Although one embodiment is to provide a bioresorbable attachment means 90 such as the sutures shown in the embodiment of FIG. 5, those of skill in the art will understand that any of the coupling means connecting the individual stent members 74 disclosed in the present application could be modified to resorb over time.

The stent assembly 46 provides an inner support frame that is generally rigid along any one of stent members 74, but which permits the stent members to move with respect to one another. In this context, "generally rigid" refers to the structural strength of the stent members 74 that is sufficient to maintain the general shape of the stent 70, but that permits some flexing along the length of the stent members. Though the stent members 74 are generally rigid, they are able to move with respect to one another. More particularly, joining the stent members 74 with the attachment means 90 creates nodes or pivot points of the valve 40 at the commissures 62 of the stent assembly 46. As will be more fully explained below with reference to FIGS. 13-16, the stent members 74 are permitted to pivot with respect to one another as they move radially inward and outward. Inward pivoting is permitted by spaces 94, seen in FIG. 5, defined between adjacent cloth-covered commissure regions 78 of each stent member 74. These regions 94 are generally triangular and gradually increase in size from the attached commissure tips to the diverging cusps.

Leaflet Configurations

Figure 7A:
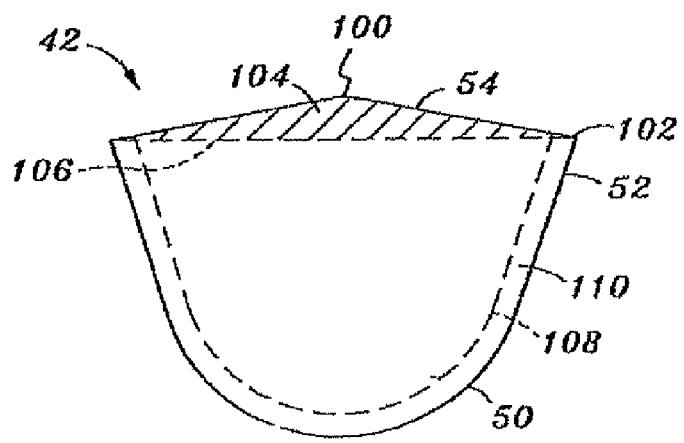
FIGS. 7A, 7B, and 7C are plan views of leaflets suitable for use in the prosthetic heart valve of the present invention.
Figure 7B:
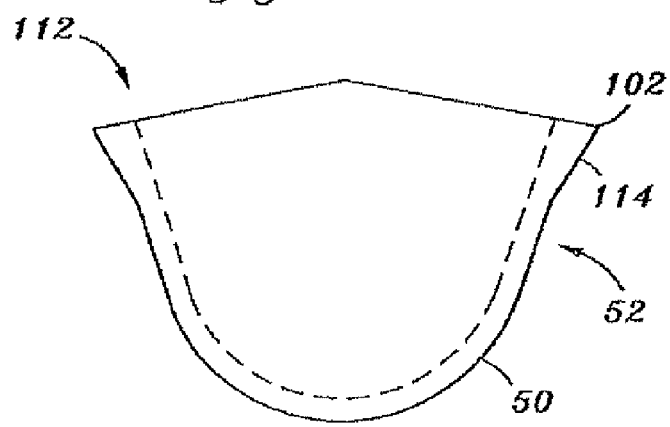
Figure 7C:
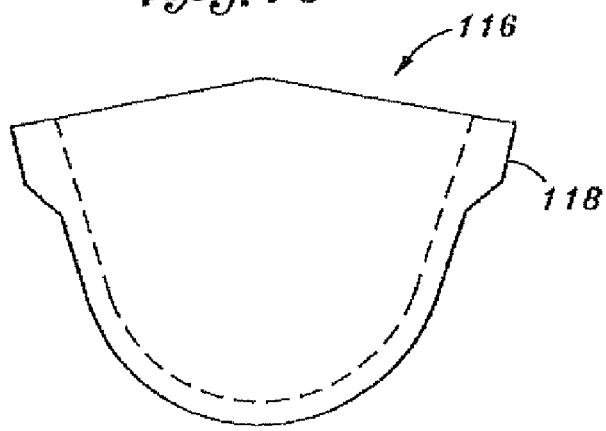

FIGS. 7A, 7B, and 7C are plan views of various configurations of leaflets 42 suitable for use in the prosthetic heart valve 40. FIG. 7A shows a leaflet 42 having the aforementioned cusp 50, commissure regions 52, and free edge 54. It will be noted that the coapting edge 54 comprises two linear portions extending from an apex 100 to outer tips 102. The two portions of the free edge 54 are angled with respect to one another and define sides of a triangular region 104 having as its hypotenuse an imaginary line 106 extending between the opposed tips 102. The triangular region 104 of each leaflet 42 is under less tension during dynamic motion of the valve 40, and helps ensure coaptation of the leaflets. That is, the leaflets 42 are generally secured along the cusp 50 and commissure regions 52, and thus the majority of each leaflet 42 is placed in stress except in the region above imaginary line 106. In this regard, an imaginary (dashed) fold line 108 defines an outer margin 110 of the leaflet 42 that is used to secure the leaflets into the valve 40. As will be clear from the discussion below, the margins 110 are sutured between the stent assembly 46 and connecting band 48 (FIG. 3), and the free edge 54 of the leaflet extends across the cylindrical region defined within the valve 40, and is generally free to move in that region. Because the triangular leaflet region 104 is relatively stress-free, it tends to roll over under the influence of fluid dynamic forces, thus helping the three leaflets to coapt and prevent valve insufficiency.

FIG. 7B shows a leaflet 112 that is substantially the same as the leaflet 42 of FIG. 7A, and thus like elements will be given the same numbers. The leaflet 112 includes a pair of generally triangular shaped commissure tabs 114 in the commissure regions 52. The tips 102 are thus spaced farther apart than in the version shown in FIG. 7A. The commissure tabs 114 are used to more securely fasten each of the leaflets to the commissures 62 of the stent assembly 46 (FIG. 3). The cloth cover 72 of the stent assembly 46 includes a flap 86 (FIG. 5) which diminishes in size in the commissure regions. The tabs 114 are thus wrapped farther around the cloth-covered stent assembly 46 in the commissure regions and sutured thereto, thus facilitating a more durable connection.

FIG. 7C is a further variation of a leaflet 116 which is, again, the same in all respects to the leaflets described above, except for somewhat trapezoidal-shaped commissure tabs 118. Again, the commissure tabs 118 help to secure the leaflets 116 in the prosthetic valve 40.

Stent/Leaflet Sub-Assembly

Figure 8:
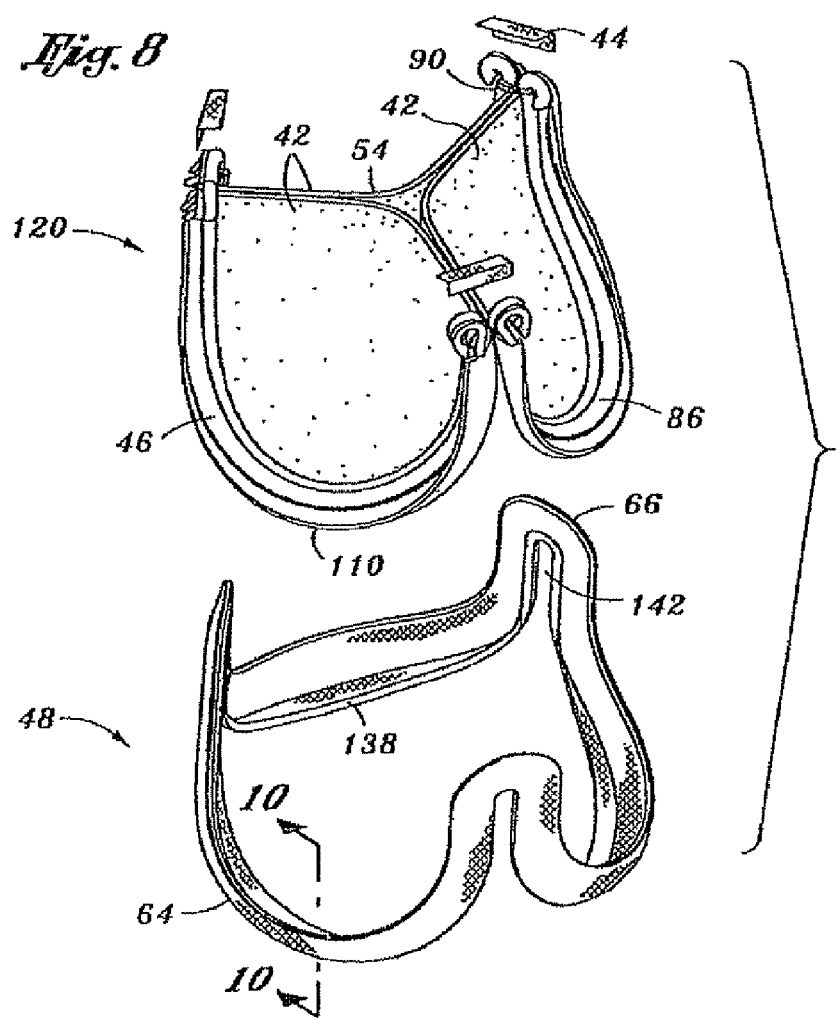
FIG. 8 is an exploded perspective view of a stent/leaflet sub-assembly and a connecting band of the prosthetic heart valve of the present invention.

FIG. 8 illustrates a stent/leaflet sub-assembly 120 in which the leaflets 42 are secured to the stent assembly 46. Preferably, leaflets 42 are pre-attached to align the free edges 54. In this manner, the free edges 54 of each two adjacent leaflets 42 extend outward in juxtaposition and are received within the triangular space 94 defined between the commissure regions 78 of the stent assembly 46 (FIG. 5). The group of leaflets 41 is thus "inserted" underneath the stent assembly 46 until the juxtaposed free edges 54 of the leaflets 42 are in close proximity below the attachment means 90. The outer margin 110 of each leaflet 42 is folded underneath the corresponding cusp 60 of the stent assembly 46. At this point, sutures or other such means attach the margins 110 to the flap 86 of the stent assembly 46. The leaflets 42 can remain attached to one another at their adjacent tips 102 (or along the free edges 54 near the tips), or can be separated for maximum valve flexibility or when the stent is designed to separate into individual stent members by bio-resorption of a commissure couple.

If either the leaflet 112 or leaflet 116 of FIG. 7B or 7C are used, the respective commissure tabs 114 or 118 are wrapped around the adjacent part of the stent assembly 46 and secured thereto. In a preferred assembly method, the leaflets 42 are simply retained in position with respect to the stent assembly 46 with temporary sutures or other such means, to permit the stent/leaflet subassembly 120 to be finally joined together with the connecting band 48 of FIG. 8.

FIG. 8 also illustrates the three alignment brackets 44 and that each has a generally L-shaped cross-section and comprises a cloth-covered inner member (not separately numbered). The inner member preferably has minimum elasticity, but is relatively thin and lightweight. One preferred material for the inner member is a polyester film such as Mylar®. The brackets 44 are preferably joined to the valve 40 at the time the stent/leaflet sub-assembly 120 and connecting band 48 are joined, and thus will be described more fully below with respect to FIG. 11.

Connecting Band

Figure 9:
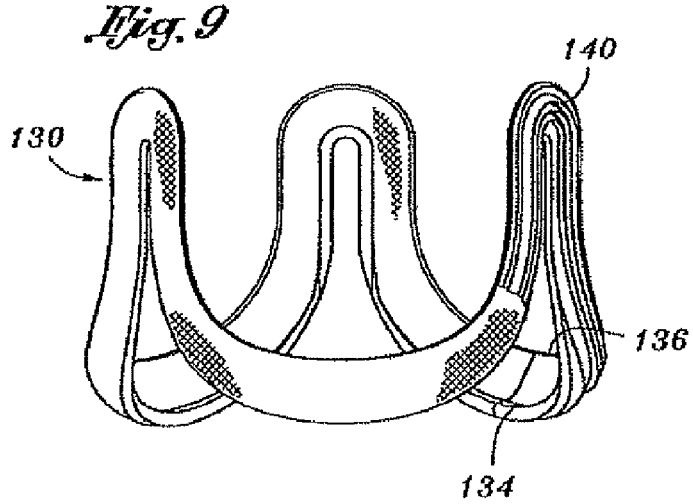
FIG. 9 is an elevational view of an inner member of the connecting band.
Figure 10:
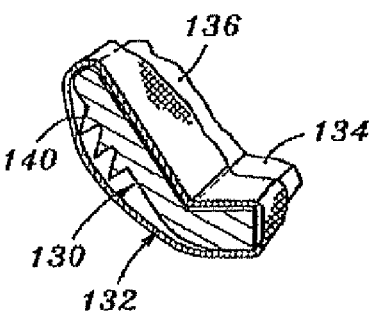
FIG. 10 is a cross-sectional view through a cusp of the connecting band shown in FIG. 8.

FIGS. 9 and 10 illustrate the connecting band 48 in more detail, comprising an inner member 130 surrounded by a cloth cover 132. As mentioned previously with respect to FIG. 3, the connecting band 48 includes three cusp portions 64 alternating with commissure portions 66, all generally formed in a tubular configuration. This shape is provided by the inner member 130, with the cloth cover 132 simply draped and sewn thereover. In a preferred embodiment, the inner member 130 is molded of silicone rubber, and the cloth cover 132 is polyterephthalate.

The inner member 130 has a varying cross sectional shape along the cusps and commissures. FIG. 10 is cross-section through one of the cusp portions 64 of the connecting band 48, and shows a region of the inner member 130 having an inner ledge 134 and upwardly angled outer free margin 136. The cloth-covered ledges 134 extend generally radially and define three stent support regions 138 of the connecting band 48, as seen in FIG. 8. The ledge 134 has its greatest radial dimension at the midpoint of each of the cusp portions 64 and gradually tapers down in size toward the commissure portions 66. Likewise, the free margins 136 form their greatest outward angle with respect to a central axis of the connecting band 48 at each cusp portion 64, and gradually re-align to be parallel to the central axis in the commissure portions 66. The cross-section of the inner member 130 at the commissure portions 66 is seen in FIG. 12B. A series of triangular shaped ribs 140 projects outward from the inner member 130. The ribs 140 are formed around the entire inner member 130, along both the cusp and commissure regions. As seen in FIG. 8, the commissure portions 66 of the connecting band 48 define generally axial gaps 142 that help permit flexing of the valve 40. It should be noted that the connecting band 48 may be discontinuous at the commissure portions 66 if the valve has bioresorbable commissures and is designed to separate into individual "leaflets."

Assembled Valve

Figure 12A:
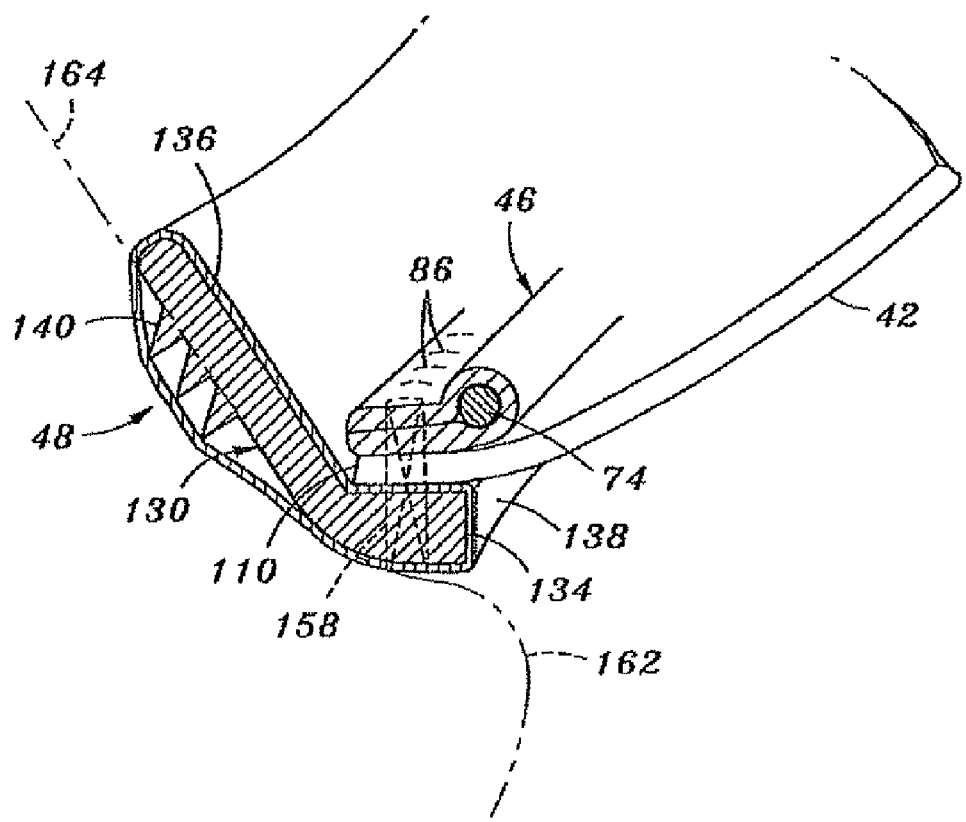
FIG. 12A is a cross-sectional view through a cusp region of the prosthetic heart valve of the present invention, taken along line 12A-12A of FIG. 11, and showing a portion of the host annulus in phantom.
Figure 12B:
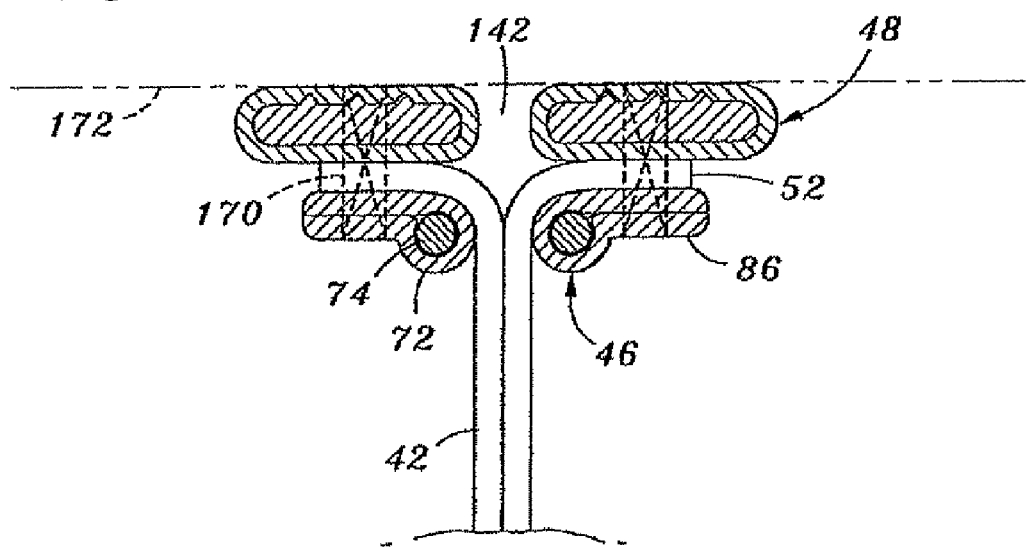
FIG. 12B is a cross-sectional view through a commissure region of the prosthetic heart valve of the present invention, taken along line 12B-12B of FIG. 11, and showing a portion of the host aortic wall in phantom.

FIG. 11 illustrates the assembled valve 40 in perspective, while FIGS. 12A and 12B show cross-sections through a valve cusp 150 and valve commissure 152, respectively. The connecting band 48 is sewn or otherwise attached to the exterior of the stent/leaflet subassembly 120. Actually, as seen in FIG. 12A, the connecting band 48 is attached underneath the stent/leaflet subassembly 120 in the cusp 150, but the free margins 136 of the connecting band are positioned to the outside of the subassembly. In addition, the alignment brackets 44 are installed with a vertical leg 156 interposed between the commissures 62 of the stent assembly 46 and the commissure portions 66 (FIG. 3) of the connecting band 48. A horizontal leg 154 of each of the alignment brackets 44 projects radially inward to cover the tips 80 of the stent assembly 46. The alignment brackets 44 help hold each two adjacent tips 80 of the three-piece stent 70 together, especially helping to prevent radial mis-alignment. The brackets also provide flat surfaces which a holder can contact, as seen best in FIG. 26.

With reference to the cross-section of FIG. 12A, the sandwiched configuration of the stent assembly 46, leaflet 42, and connecting band 48 can be seen. More specifically, the cloth flap 86 of the stent assembly 46 aligns with the leaflet margins 110, which in turn rest on the stent supports 138. A series of suture stitches 158 are used to secure these elements together. Preferably, the flap 86 terminates at the same location as the margin 110 of each leaflet 42, and at the corner defined in the connecting band 48 between each ledge 134 and free margin 136. The radially innermost wall of the ledge 134 is preferably inward from the stent member 74. This construction helps prevent the stent 70 from migrating downward with respect to the connecting band 48.

The host annulus 162 is seen in phantom with the aortic wall 164 continuing upward therefrom. It can be readily seen that the angled shape of the cusp portions 64 of the connecting band 48 conform nicely to the host annulus region. The triangular ribs 140 provide volume at the free margins 136 of the connecting band 48 to facilitate connection to the natural tissue; in other words, more volume provides more of a "bite" for the surgeon to secure the band 48 with a suture needle. Although the conventional means for attaching the valve 40 to the host tissue is with sutures, which are not shown, the present invention should not be construed as limited to being implanted with sutures and other means such as staples, adhesives, and the like could be used.

Now with reference to FIG. 12B, the assembly of the valve components in the commissure region is seen. The commissure edges 52 of each of the leaflets 42 are sandwiched in between the stent assembly 46 and connecting band 48. More particularly, the commissure edges 52 are sandwiched between the flaps 86 and the generally planar commissure portions 66 of the connecting band 48 (FIG. 8). Sutures 170 are provided to join these elements together. Again, the commissure edges 52 preferably terminate at the same location as the flaps 86. FIG. 12B also illustrates the gap 142 provided in the commissure regions of the connecting band 48, and the lack of structural connection between the two sides of each valve commissure 152.

FIG. 12B shows in phantom a portion of the aortic wall 172 to which the commissures 152 of the valve 40 are attached. Again, the particular attachment means is not shown, but the connecting band 48 is traditionally sutured to the wall 172.

Dynamic Motion of the Prosthetic Heart Valve

Figure 13:
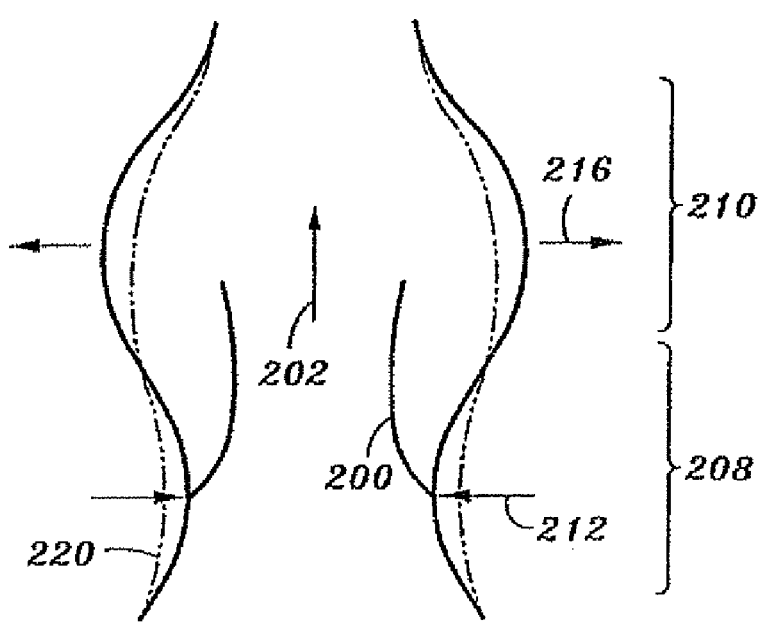
FIG. 13 is a schematic view showing relative movement of the aortic and annulus walls during systolic flow.
Figure 15:
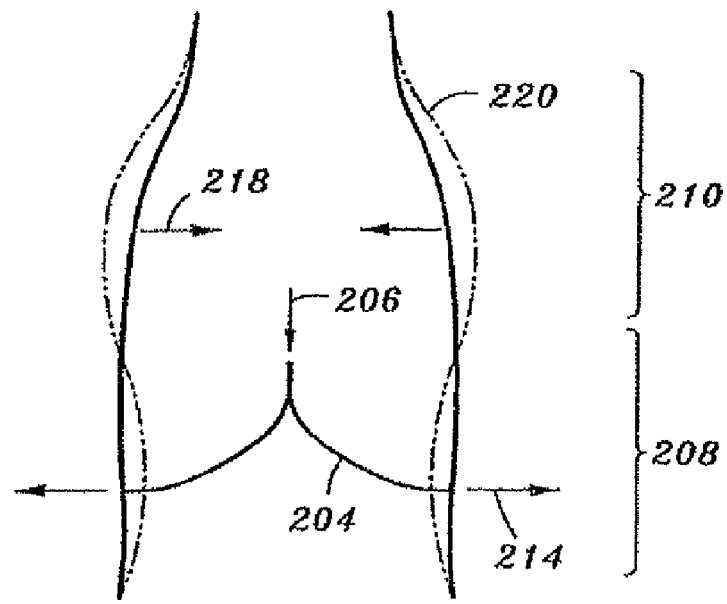
FIG. 15 is a schematic view showing relative movement of the aortic and annulus walls during diastolic flow.

FIGS. 13 and 15 illustrate a conduit portion of a heart in the region of the aortic valve and relative motions of the conduit walls during systole and diastole, respectively. In particular, FIG. 13 shows an open valve 200 and systolic blood flow 202, while FIG. 15 shows a closed valve 204 and diastolic back flow of blood 206. As described with respect to FIGS. 1 and 2, the regions around the aortic valve can be generally separated into an annulus region 208 and a sinus region 210.

As mentioned previously, the annulus region 208 is expected to contract during the systolic phase, as indicated by the arrows 212 in FIG. 13, and expand during the diastolic phase, as indicated by the arrows 214 in FIG. 15. Conversely, the sinus region 210 is expected to expand during the systolic phase, as indicated by the arrows 216 in FIG. 13, and is expected to contract during the diastolic phase, as indicated by the arrows 218 in FIG. 15. The movements of the conduit walls are shown with respect to a neutral or relaxed position 220, and may be exaggerated from the true movements. Also, as mentioned above, these movements are educated guesses and may be different for some, if not most patients. However, the flexible heart valve of the present invention accommodates all variations of such movements.

FIGS. 14 and 16 schematically illustrate the synchronous movement of the prosthetic valve 40 of the present invention with respect to the movements of the host tissue in systolic and diastolic phases as seen in FIGS. 13 and 15. To simplify this explanation, FIGS. 14 and 16 only illustrate the stent 70 of the present invention, which as previously described acts as a limitation to movement of the entire valve 40 and fairly represents movement of the entire valve.

Figure 14A:
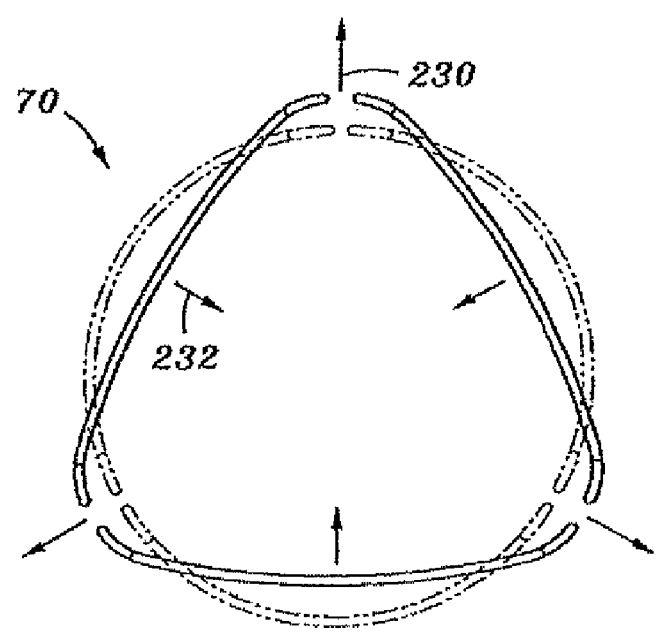
FIG. 14A is a plan view of only the stent members of the prosthetic valve flexed in accordance with the anatomical motions during systole shown in FIG. 13.
Figure 14B:
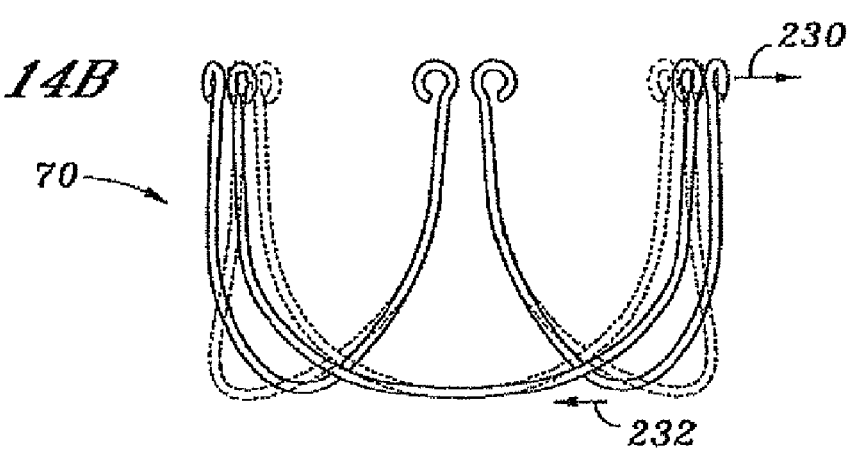
FIG. 14B is an elevational view of the stent members flexed in accordance with the anatomical motions during systole shown in FIG. 13.
Figure 16A:
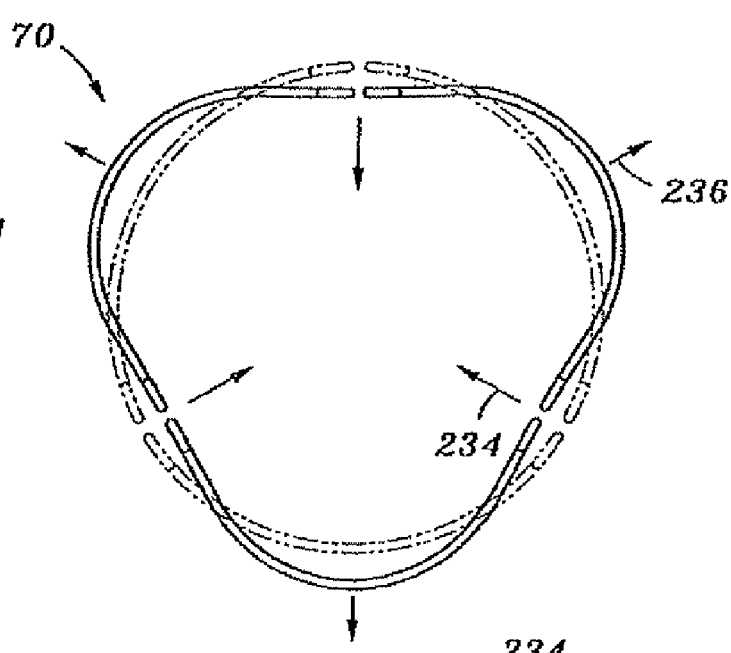
FIG. 16A is a plan view of only the stent members of the prosthetic valve flexed in accordance with the anatomical motions during diastole shown in FIG. 15.
Figure 16B:
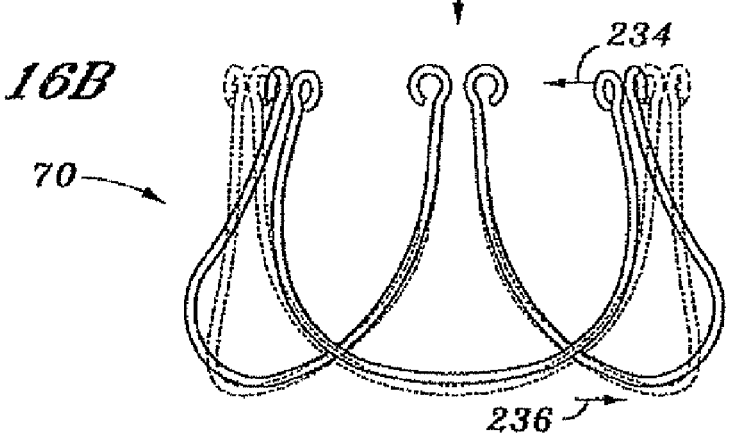
FIG. 16B is an elevational view of the stent members flexed in accordance with the anatomical motions during diastole shown in FIG. 15.

With reference to FIGS. 14A and 14B, during systole the valve experiences outward commissure movement, as indicated by the arrows 230. At the same time, the valve experiences inward movement at the cusps, as indicated by the arrows 232. During diastole, in contrast, and as seen in FIGS. 16A and 16B, the valve experiences inward commissure movement, as indicated by the arrows 234. At the same time, the valve experiences outward movement at the cusps, as indicated by the arrows 236.

Alternative Stents

FIGS. 17-19 illustrate an alternative stent assembly 250 comprising an inner stent 252 and an outer cloth cover 254. As with the earlier stent assembly 46, the stent assembly 250 includes alternating cusps 256 and commissures 258. As best seen in FIG. 18, the stent 252 includes three separate stent members 260 having arcuate commissure tips 262 that are curved toward one another. A generally disk-shaped commissure housing 264 encompasses the adjacent commissure tips 262, retaining the stent members 260 together while permitting relative pivoting.

FIG. 19 illustrates two adjacent commissure tips 262 and the commissure housing 264 exploded into a male housing portion 266 and a female housing portion 268. The housing portions are so named because they are joined together through interference between a button 270 of the male housing portion 266 and an aperture 272 on the female housing portion 268. Each portion of the commissure housing 264 includes a circular groove 274 for receiving the arcuate tips 262. The grooves 274 combined to form a circular channel having an axis 276 within which the arcuate tips 262 are received and can slide. When assembled together, the commissure housings 264 thus provide nodes of rotation for each of the stent members 260.

Figure 20A:
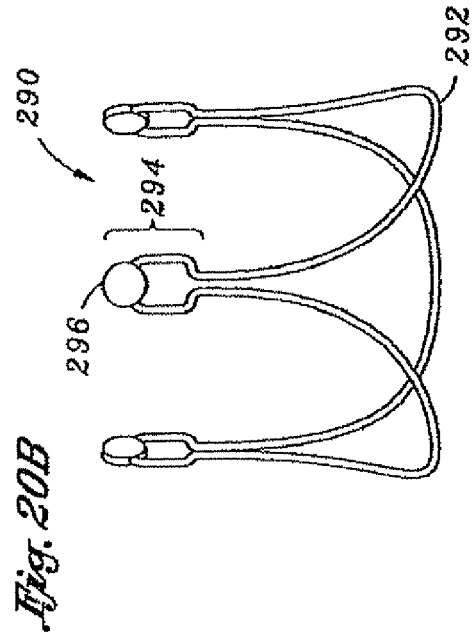

FIG. 20A illustrates an alternative stent 280 suitable for use in a heart valve of the present invention. The stent 280 includes three stent members 282, each having commissures with a flex region 284 and tips 286. The tips 286 of adjacent stent members 282 are secured together by sutures or other suitable means (not shown). The flex regions 284 comprise sections of each stent member 282 which are bent away from each other. The stent members 282 can thus pivot with respect to one another about the connected tips 286. Upon inward movement of the stent members 282, a fulcrum 288 is created by interaction between the stent members at the lower end of the flex region 284. The relative flexibility in inward or outward movement of the stent members 282 can be modified by selection of the cross sectional size and shape of the stent members, and overall configuration of the flex region 284.

Figure 20B:
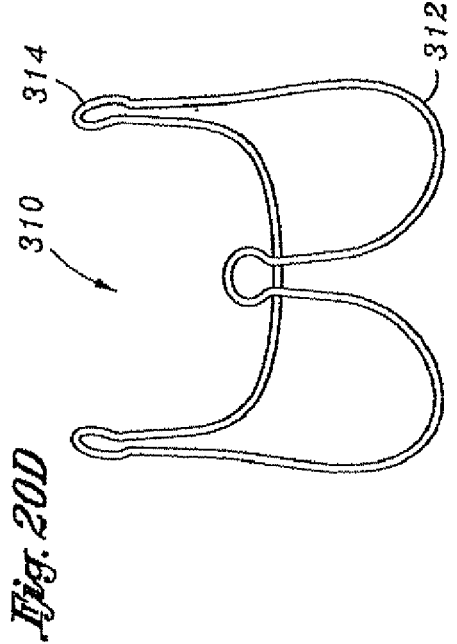

FIG. 20B illustrates a second alternative stent 290 suitable for use in a heart valve of the present invention. The stent 290 includes three wires 292 and has commissure regions 294 formed by bent ends of the wires and a junction member 296. In this embodiment, the junction member 296 either rigidly holds the terminal ends of each of the wires 292, or permits the wires to slide or otherwise flex with respect to one another. If the wires are rigidly attached to the junction member 296 the shape of the wires in the commissure region 294 reduces stress risers in bending.

Figure 20C:
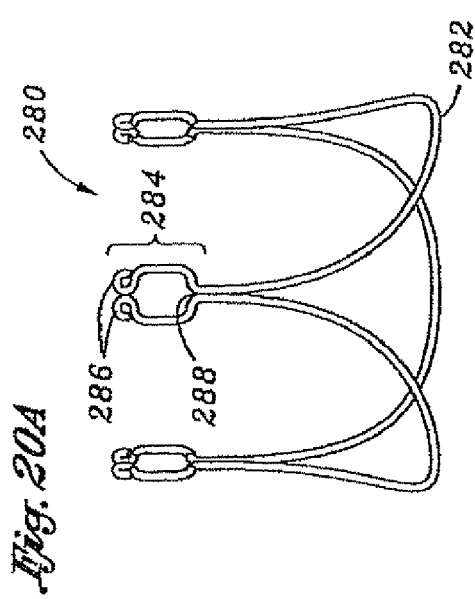
Figure 20D:
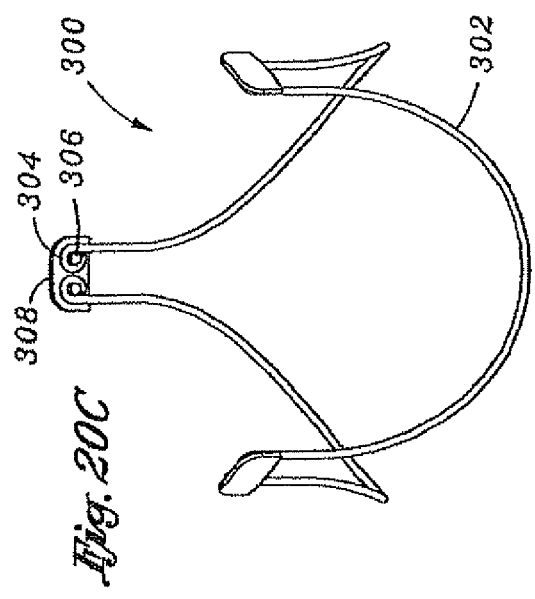

FIG. 20C illustrates a third alternative stent 300 suitable for use in a heart valve of the present invention. The stent 300 comprising three separate wires 302 terminating at circular commissure tips 304. Each of the commissure tips 304 is rotatably fastened around a pin 306 provided on a junction plate 308 common to adjacent wires 302. In this manner, the tips 304 remained located close to one another, while the cusps of the wires 302 can pivot in and out.

FIG. 20D illustrates a fourth alternative stent 310 suitable for use in a heart valve of the present invention. The stent 310 is made in one piece with a series of alternating cusps 312 and commissures 314. The commissures 314 comprising a nearly 360° bend in the stent 310 which permits each cusp 312 to easily flex with respect to the other cusps.

FIG. 20E illustrates a fifth alternative stent 320 suitable for use in a heart valve of the present invention. The stent 320 comprises three wire-like stent members 322, adjacent ones of which are joined together at commissure regions 324 by a U-shaped coupling 326 and a pair flexible sleeves 328. FIG. 21 is a detail of one of the commissure regions 324 showing in hidden lines the adjacent ends of the coupling 326 and stent members 322. The couplings 326 are preferably sized with the same diameter as the stent members 322, and the sleeves 328 are tubular with a constant diameter lumen. The sleeves 328 may be made of silicone, or a flexible polymer such as polyurethane or the like. Other flexible interfaces such as sleeves 328 are contemplated, such as, for example, a single block of silicone into which the commissure regions 324 of the stent members 322 are molded.

FIG. 22 is a detailed view of a commissure region 330 of a still further alternative stent suitable for use in a heart valve of the present invention. The stent is made in one piece with adjacent cusps 332 being joined by a coil spring tip 334. Again, great flexibility is provided by the coil spring tips 334 to enable relative motion of the cusps 332. The amount of flexibility is selected as in any spring by varying the material, cross-sectional size and shape, and number of turns of the spring.

Valve Holder

FIGS. 23-26 illustrate a preferred holder 350 useful for implanting the flexible heart valve 40 of the present invention. As the heart valve 40 is relatively flexible, the holder 350 must provide adequate support to insure a stable platform for the surgeon to position the valve for attachment to the natural tissue. In other words, because the flexible prosthetic heart valve 40 of the present invention exhibits alternating cusps and commissures in a generally cylindrical configuration that are adapted to move radially in and out with respect to one another, the holder 350 desirably provides rigid structure for maintaining a fixed shape of the valve during implantation. In addition, the holder 350 must include structure to allow quick release from the valve 48 after the valve is implanted.

Figure 23:
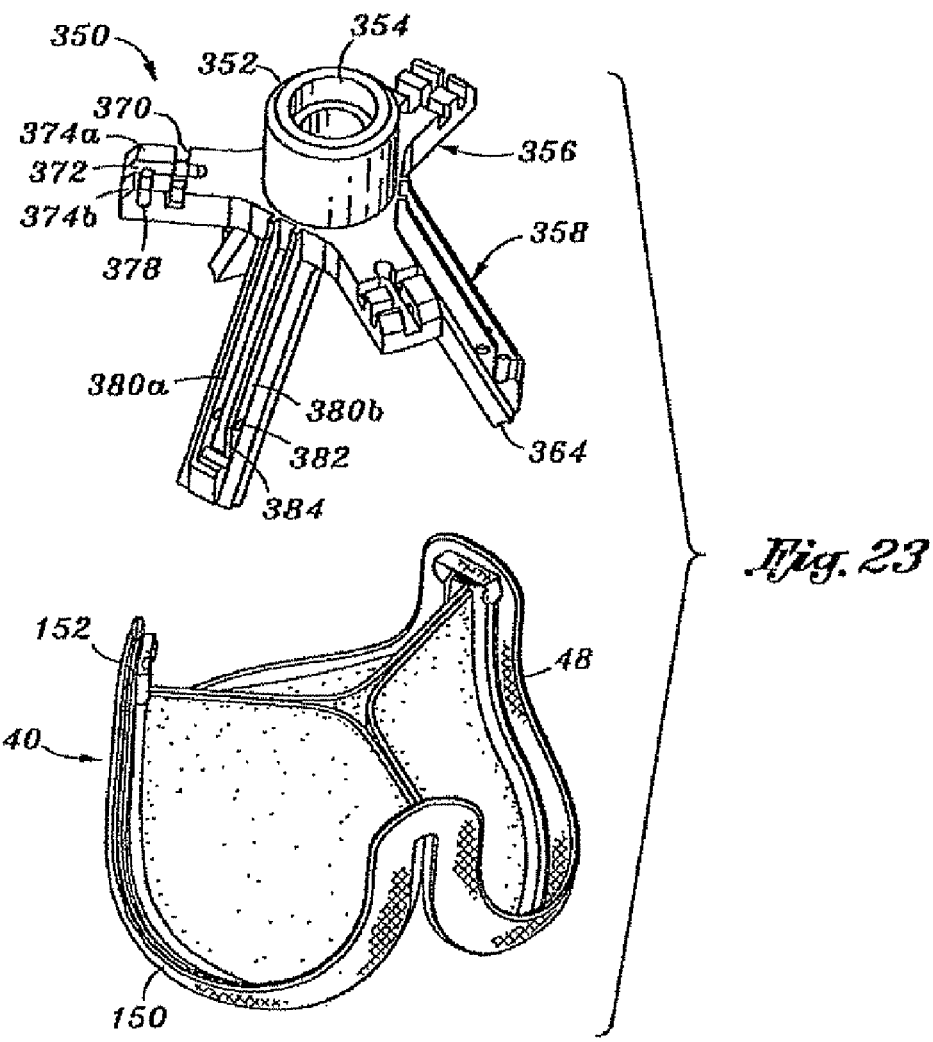
FIG. 23 is an exploded perspective view of the prosthetic heart valve of the present invention and a holder used during implantation of the valve.

As seen in FIG. 23, the holder 350 comprises a proximal handle socket 352 having an inner bore 354 for receiving the distal end of a handle (not shown). The socket 352 may be provided with internal threads, or other such quick-release coupling structure to facilitate handle connection and disconnection. The holder 350 has three radially outwardly-directed commissure legs 356, and three outwardly and downwardly angled cusp legs 358. Consistent with the distribution of the cusps 150 and commissures 152 of the valve 40, the commissure legs 356 are oriented 120° apart, and the cusp legs 358 are oriented 120° apart, with the three commissure legs being offset with respect to the three cusp legs by 60°.

Figure 24:
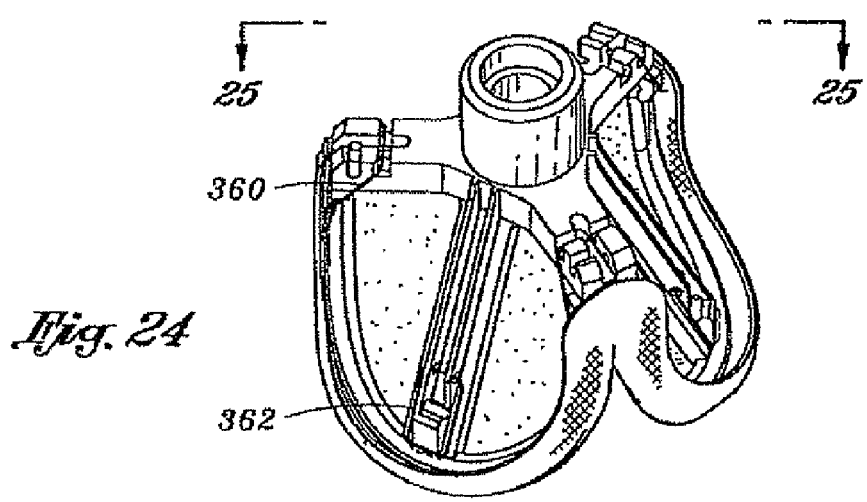
FIG. 24 is a perspective view of the holder coupled to the valve.
Figure 25:
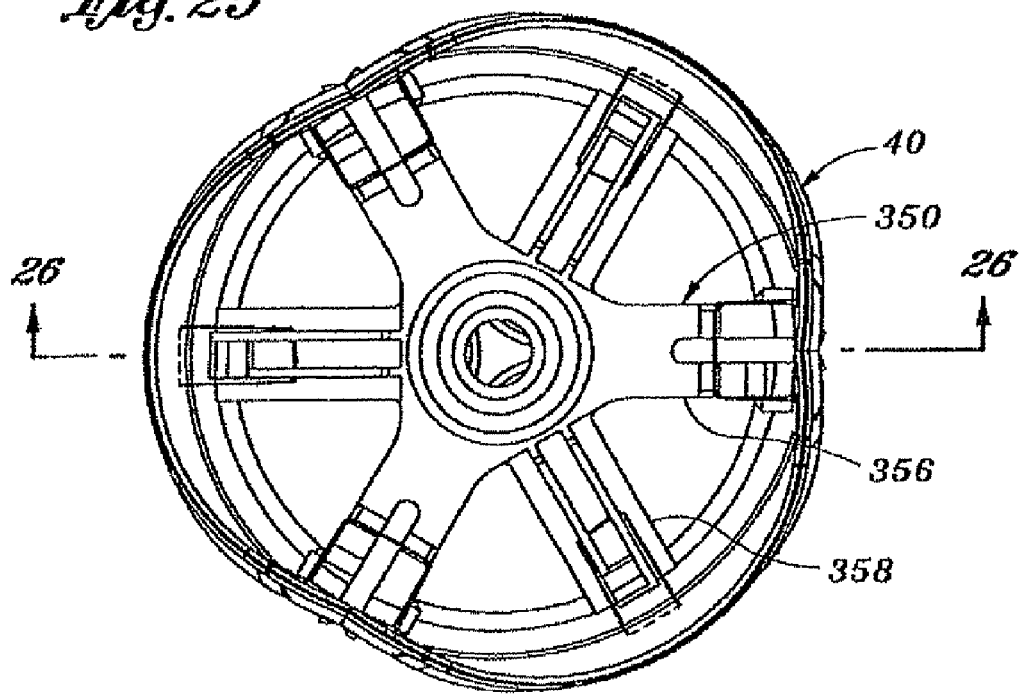
FIG. 25 is a top plan view of the holder coupled to the valve.
Figure 26:
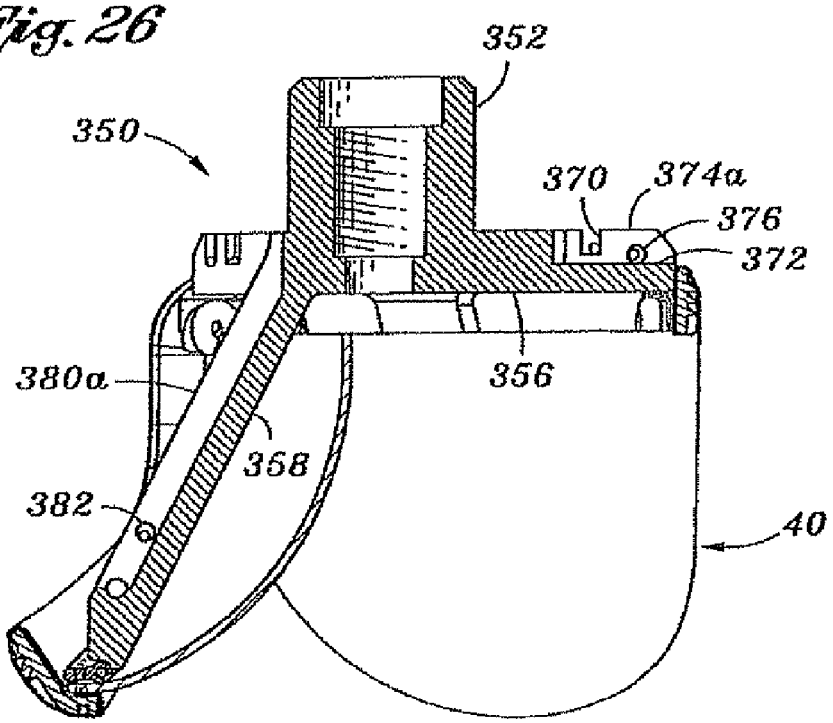
FIG. 26 is a cross-sectional view through the holder and valve, taken along line 26-26 of FIG. 25.

As seen in FIG. 24, each of the commissure legs 356 extends outward from the handle socket 352 into proximity with one of the valve commissures 152 and is secured thereto with an upper suture 360. Likewise, each of the cusp legs 358 extends outward and downward from the handle socket 352 into proximity with a midpoint of one of the valve cusps 150, and is secured thereto with a lower suture 362. The lower end of each cusp leg 358 includes a concavity for mating with the corresponding rod-like stent member 74, as seen in FIG. 26. In this manner, each of the cusps 150 and commissures 152 of the valve 40 is securely held in relation to the others, thus facilitating implantation by the surgeon.

Details of the commissure legs 356 will now being described with reference to FIGS. 23 and 26. Each commissure leg 356 extends outward from the handle socket 352 in a generally rectangular cross-section interrupted by an upwardly-facing inner notch 370 oriented cross-wise to the leg. And upwardly-facing radial channel 372 having a depth of approximately half of each commissure leg 356 extends from about the inner notch 370 to the outermost end of the leg. The inner notch 370 is not quite as deep as the channel 372, as seen in FIG. 26. The radial channel 372 divides the upper portion of each commissure leg 356 into two walls 374a, 374b. An eyehole 376 is formed in one of the walls 374a, and a corresponding outer notch 378 is formed in the other wall 374b aligned with the eyehole. The outer notch 378 is also not quite as deep as the channel 372.

With reference to FIGS. 24 and 26, the upper suture 360 is preferably tied to the eyehole 376 in the first wall 374a. The suture 360 then passes across the channel 372, through the outer notch 378, and is passed along the inner notch 370, again traversing the channel 372. The suture 368 is then passed through a suture-permeable portion of the valve commissure 152, such as through the connecting band 48. After passing through the commissure 152, the suture 360 is again looped through one or both of the notches 370, 378 and re-tied to the eyehole 376. By proper threading of the upper suture 360, each commissure 152 can be secured to the commissure leg 356 and easily released by inserting a scalpel blade into the radial channel 372 to sever the portions of the suture therein.

Details of each cusp leg 358 can be seen in FIGS. 23 and 26. A pair of longitudinal rails 380a, 380b are provided on the outer side of each cusp leg 358. Toward the lower end of the rails 380a,b, a pair of aligned eyeholes 382 provide anchoring locations for the lower suture 362. A scalpel guide or relief 384 is formed in one of the rails 380b. As seen in FIG. 24, the lower suture 362 extends downward from the eyeholes 382, passes through a suture-permeable portion of the cusp 150, and is then returned and secured to the eyeholes 382. The relief 384 exposes a portion of the lower suture 362 for severing by the surgeon using a scalpel blade. It will thus be understood that the holder 350 can be quickly released from the valve 40 by a series of six scalpel strokes, with each of the sutures 360, 362 remaining attached to the holder 350 and being withdrawn from the valve 40 as the holder is withdrawn.

Figure 27A:
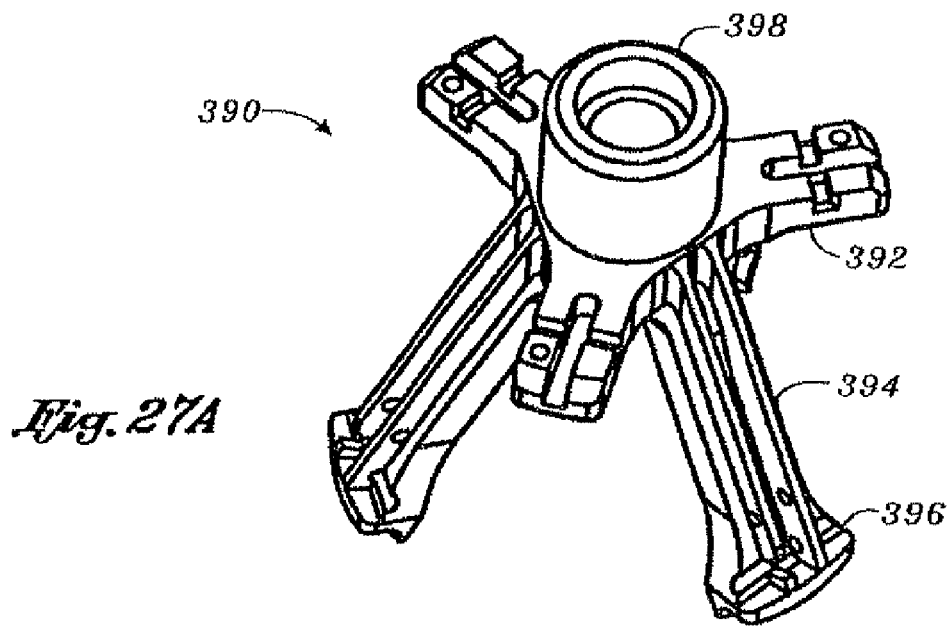
FIGS. 27A ad 27B are perspective views of an alternative holder for the prosthetic heart valve of the present invention used during implantation of the valve.
Figure 27B:
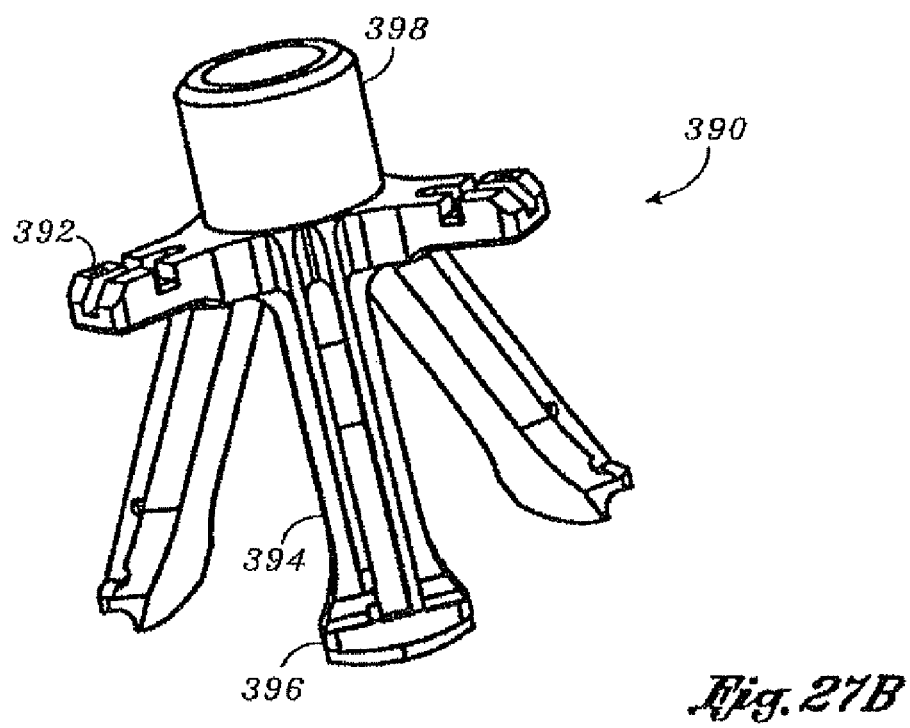

FIGS. 27A and 27B illustrate an alternative holder 390 useful for implanting the flexible heart valve 40 of the present invention. The holder 390 is substantially similar to the holder 350 described above, but the ends of each of a plurality of rigid legs for attaching to the valve cusps are flared, or, more precisely, each lower leg has a width from a hub to a terminal end that is greatest at the terminal end to provide more surface area to contact the corresponding valve cusp. That is, the holder 390 includes a plurality of upper legs 392 having a generally constant width, and a plurality of lower legs 394 having flared ends 396, the legs extending from a central hub 398. Again, the upper legs 392 extend radially outward to connect to the valve commissures 152, and the lower legs 394 angle radially outward and downward to connect to the valve cusps 150. The flared ends 396 impart greater stability to the flexible valve 40 during implantation, especially helping to prevent movement of the cusps 150. In addition, the legs 194 remain fairly narrow until the flared ends 396 to maintain good visibility through the spaces between the plurality of legs. That is, for example, the surgeon can continue to view the valve leaflets 42 between the legs as a check on valve orientation.

Figure 28:
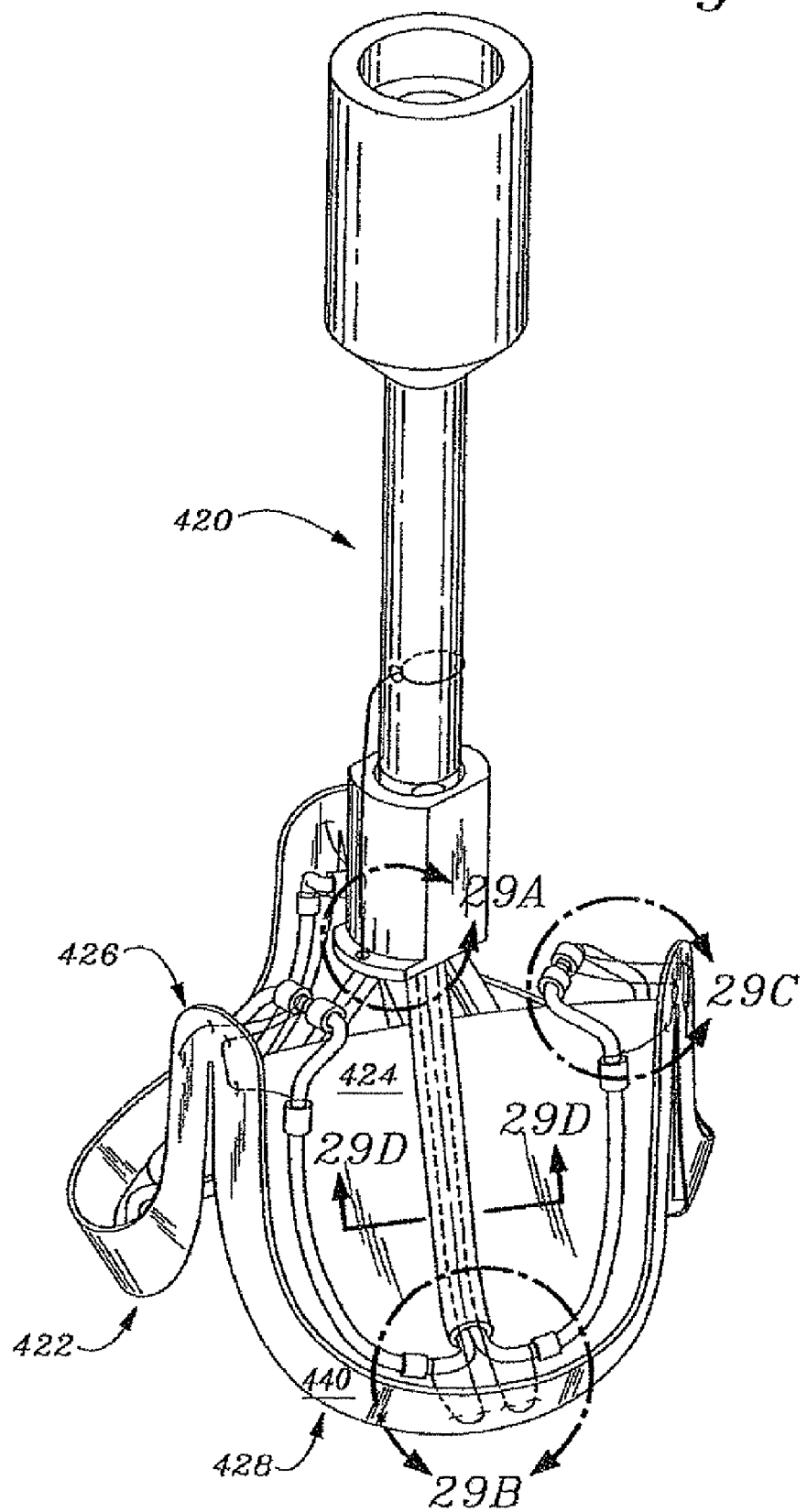
FIG. 28 is a perspective view of an exemplary holder attached to a flexible heart valve of the present invention having cusp and commissure supporting sections.

FIG. 28 illustrates a further holder 420 of the present invention attached to a flexible heart valve 422. (It should be noted that in FIGS. 28-33, the valve 422 is only schematically shown so as to better illustrate the holder 420 structure.) As before, the valve 422 includes multiple leaflets 424 joined together at adjacent juxtaposed valve commissures 426 that are generally axially aligned and commonly disposed about a valve axis (not illustrated) and are each disposed between adjacent curvilinear valve cusps 428. The holder 420 is shown without the valve 422, assembled in FIG. 30 and exploded in FIG. 31.

As described and shown above in previous embodiments, the holder 420 attaches to and securely maintains each of the cusps 428 and commissures 426 of the flexible valve 422 in relation to the others, thus facilitating implantation by the surgeon. In this regard, the holder 420 may be relatively rigid to support and define the valve shape against inadvertent external forces during the implant process. Optionally, the holder 420 may be somewhat flexible and resilient so to enable deliberate manipulation by the surgeon desiring to view a portion of the heart anatomy occluded by the valve 422. For example, one of the commissures 426 or cusps 428 may be radially bent inward along with the adjacent portion of the holder 420 so as to view the underlying annulus. Various flexible constructs of the holder 420 are contemplated, which will be further described below.

For orientation purpose, the coordinate axes of the holder 420 and attached valve 422 are: the axial direction or axis generally along the flow path through the valve and coincident with a central handle for the holder; the radial direction with respect to the axis; and the circumferential or tangential direction also with respect to the axis. Most tissue heart valves include three commissures 426 and three cusps 428 that mimic the natural valve peripheral shape. The three commissures 426 are generally evenly circumferentially disposed about the flow axis (i.e., 120° apart), with the three cusps 428 being circumferentially disposed midway between each two commissure. The holder 420 of the present invention desirably maintains the axial and circumferential orientation of the valve, while permitting some radial flexure. The need for such flexure depends on the implantation technique used, and will be described below.

Figure 29A:
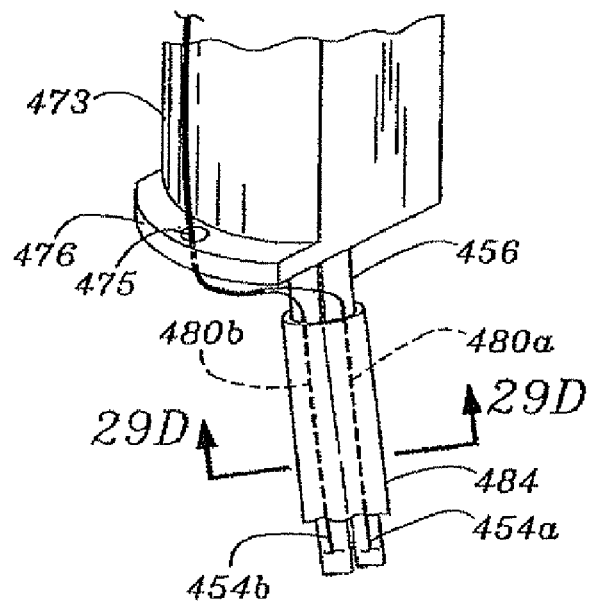
FIGS. 29A-29D are detail views of portions of the combined holder and heart valve of FIG. 28.
Figure 29C:
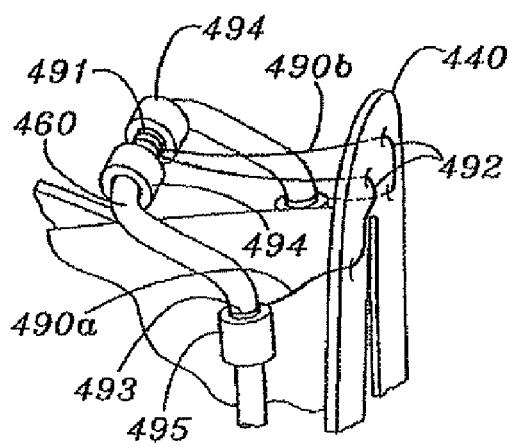
Figure 29D:
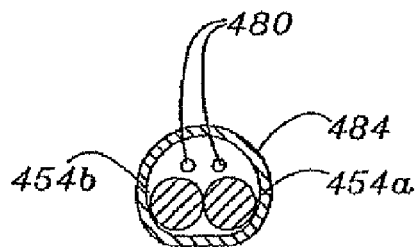
Figure 29B:
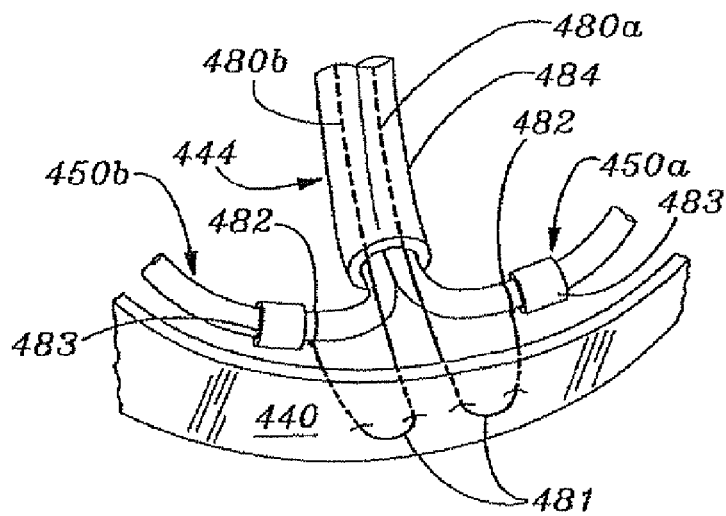
Figure 30:
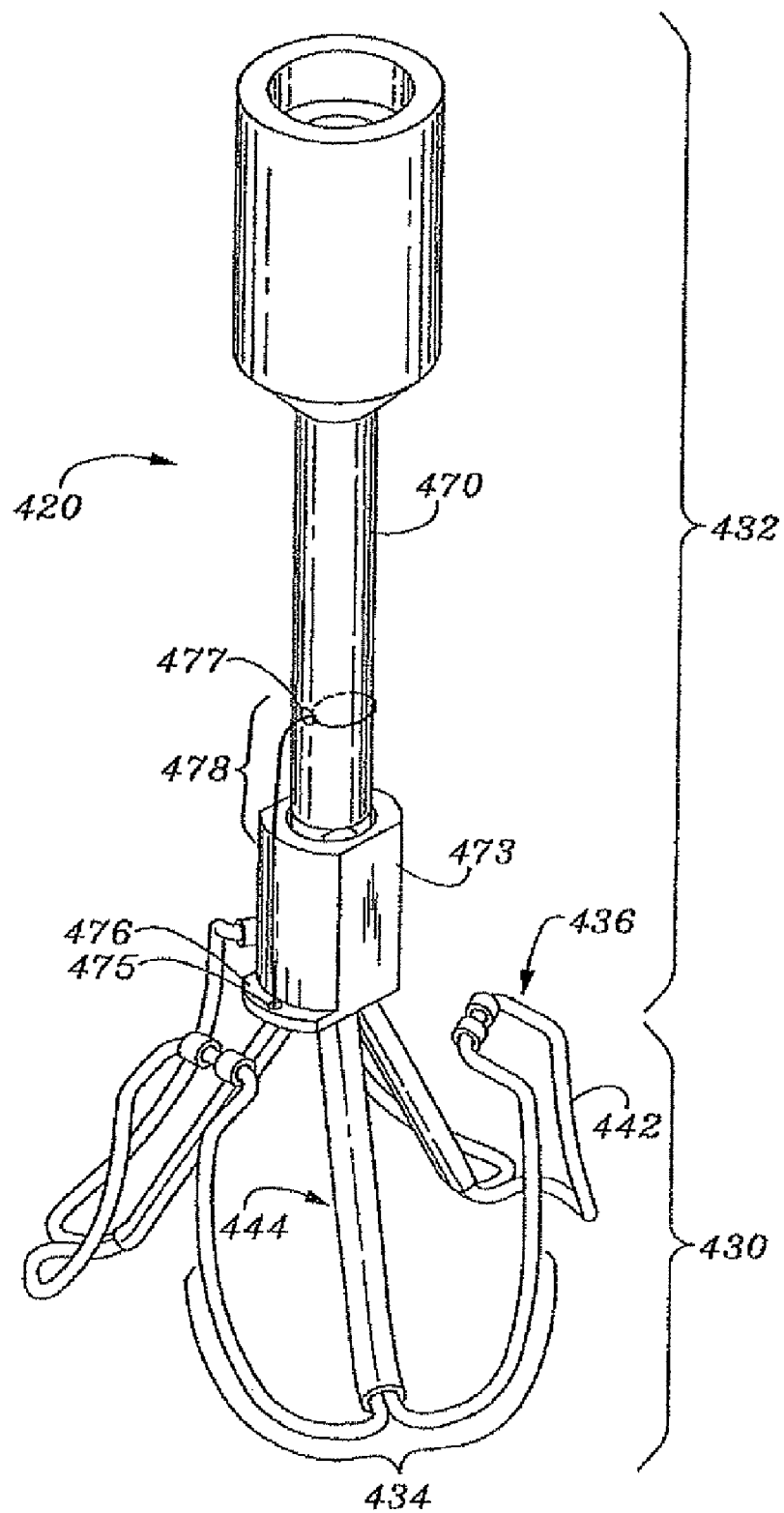
FIG. 30 is an assembled perspective view of the valve holder of FIG. 28.

With reference to FIGS. 28-31, and in particular FIG. 30, an exemplary holder 420 includes a valve contacting portion 430 and a handle connector 432. The valve contacting portion 430 includes a plurality of cusp supports 434 arranged to contact the heart valve 422 generally along the valve cusps 428, and a plurality of commissure supports 436 connected to the cusp supports and arranged to abut the valve commissures 426. In a preferred embodiment, the commissure supports 436 are radially flexible enabling the valve commissures 426 to be flexed inward while in contact therewith; for example, the commissure supports 436 may be made of a resilient, biocompatible material such as Nitinol.

The cusp supports 434 are formed in the same curve and dimensions as the associated flexible heart valve 420, as seen in FIG. 28. The valve 420 shown includes an outer sewing band 440 and the cusp supports 434 are shaped to abut and contact, or at least closely conform to, the inner surface of this band when the holder is positioned on the outflow side of the leaflets 424. Through attachment structure to be described below, the cusp supports 434 and outer sewing band 440 at the valve cusps 428 are coupled so as to reinforce the flexible valve 422 at those locations. It should be understood that other flexible heart valves than the version illustrated may be delivered using the exemplary holder 420, or other holders illustrated herein, and that the cusp supports 434 may attach to structure other than the sewing band 440, such as to a cloth-covered frame or stent structure.

Figure 31:
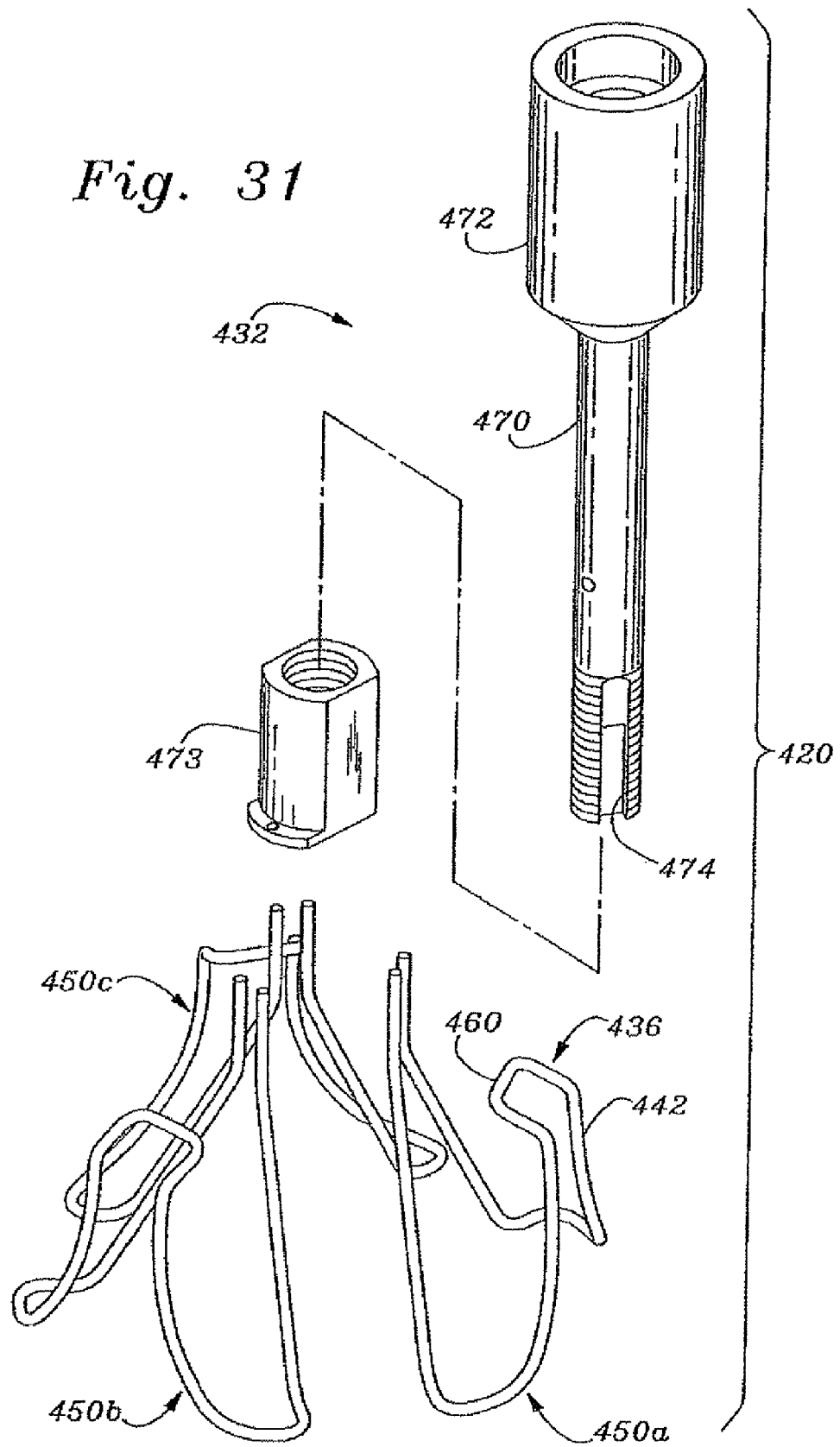
FIG. 31 is an exploded perspective view of the valve holder of FIG. 28.

As illustrated best in FIGS. 30 and 31, a plurality of wire-like elements define the valve contacting portion 430 of the exemplary holder 420, desirably forming a plurality (preferably three) of alternating and contiguous curvilinear cusp supports 434 and commissure supports 436. There is no discrete transition between the alternating supports 434, 436, the curvilinear cusp supports eventually straightening and becoming oriented generally axially at intermediate sections 442 prior to the commissure supports.

The contiguous cusp supports 434 and commissure supports 436 join to the handle connector 432 via a plurality of legs 444. The legs 444 emanate radially outward from the centrally located distal end of the handle connector 432 to several locations on the valve contacting portion 430. For example, as shown in FIG. 30, three legs 444 may extend between the handle connector 432 and a mid-point of each cusp support 434, although the legs may also extend to the commissure supports 436 or both. The common connection of the three legs 444 at the distal end of the handle connector 432 enables positioning of the holder 420 (and attached valve 422) to be controlled by manipulation of the handle connector.

Figure 32:
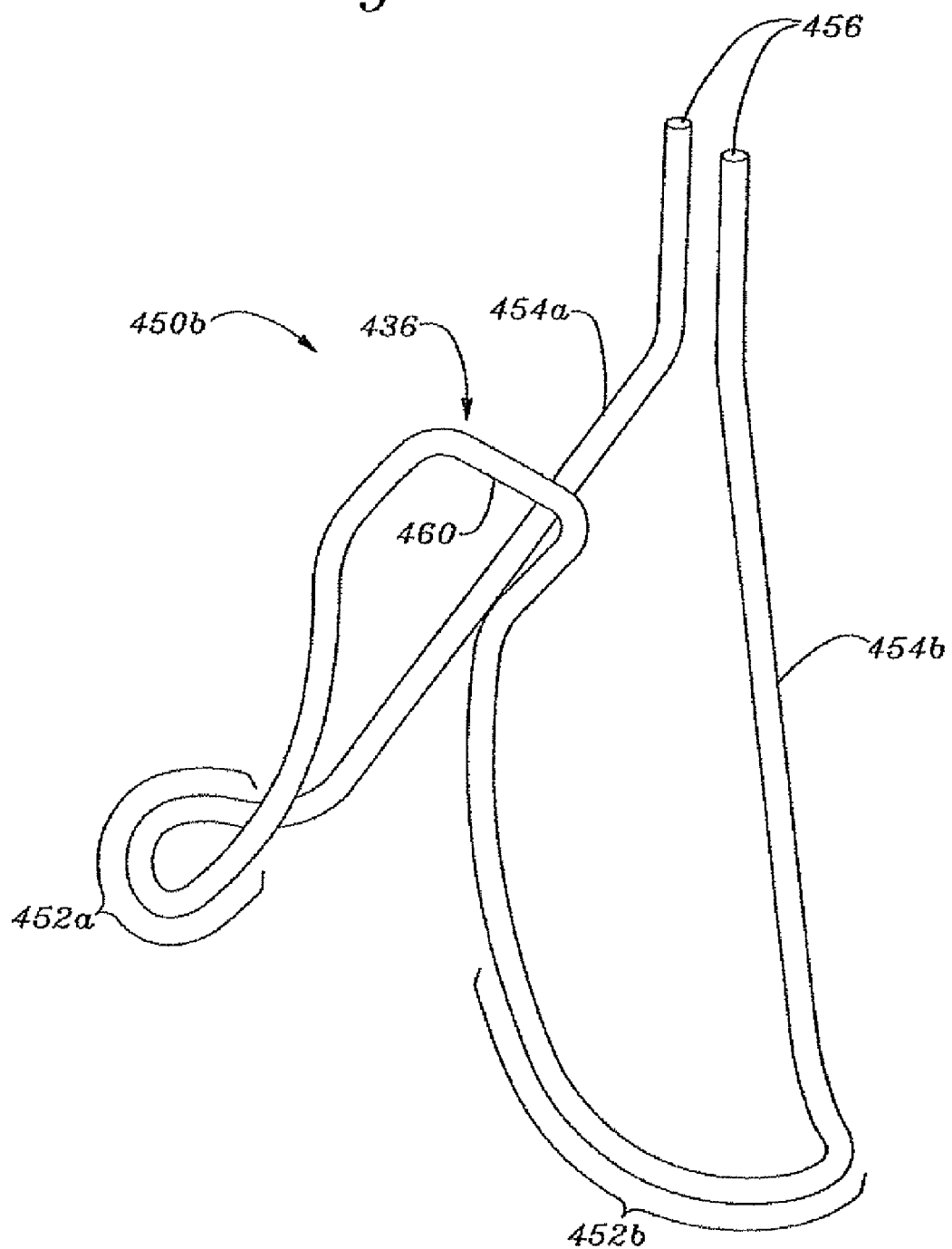
FIG. 32 is a perspective view of one piece of a valve contacting portion of the valve holder of FIG. 28.

FIGS. 31 and 32 best illustrate the exemplary wire-like valve contacting portion 430 and associated legs 444 formed in three pieces 450a, 450b, 450c. With specific reference to FIG. 32, each one of the three pieces 450 comprises two halves 452a, 452b of adjacent cusp supports 434 and a commissure support 436. Each of the three pieces 450 also has two leg halves 454a, 454b extending radially inward from a respective cusp support half 452a or 452b. When the three pieces 450a, 450b, 450c are positioned evenly about an axis, each pair of adjacent leg halves 454 makes up one of the holder legs 444 and two adjacent cusp support halves 452a, 452b in different holder pieces define a whole cusp support 434. Each leg half 454 terminates at a free end 456 that extends generally axially and can be easily joined along with the other similarly aligned free ends to the handle connector 432. Preferably, each of the three pieces 450 is identical and the free ends 456 coincide generally along a central axis, so that the handle connector 432 lies along the central axis as well. Each commissure support 436 includes a leaflet guard section 460 that is bent radially inward from the adjacent intermediate sections 442. The function of the leaflet guard sections 460 will be described below with respect to the structure used to attach the holder 420 to the valve 422.

FIG. 31 illustrates the handle connector 432 having a proximal stem 470 and handle coupling 472 exploded from a distal hub member 473. Alternatively, of course, the entire handle connector 432 may be one piece, and formed by molding, for example. The coupling 472 includes structure such as an internally threaded socket for receiving a valve delivery handle (not shown). The stem 470 has a length suitable to enable a surgeon to manually grasp it and manipulate the holder 420 and attached valve 422. Desirably, the length of the handle connector 432 is at least one inch, and preferably between one and four inches. The handle connector 432 is made of a material that is capable of being stored in a solution in which the valve 422 is stored between manufacture and usage. For example, typical bioprosthetic valves may be stored for periods of years in glutaraldehyde, and the handle connector 432 may be made of a polymer that can withstand such storage conditions, such as Delrin. The distal hub member 473 may be internally threaded for mating with external threads on the stem 470, wherein mutual cooperation of the two elements may serve to clamp the free ends 456 of the holder pieces together, such as having a bifurcated distal end 474 of the stem that constricts upon mating with the hub member. Of course, numerous other ways to secure the free ends 456 to the handle connector 432 are possible, including molding as a homogeneous structure.

FIGS. 28 and 29A-29D illustrate an exemplary system for removably securing the holder 420 to the valve 422 using sutures. In one embodiment, at least the commissure supports 436 are secured to the valve commissures 426 in a manner that permits easy release, but preferably both the commissure supports and cusp supports 434 are so connected. Sutures are preferred as the means for attaching various points on the holder 420 with coincidental points on the valve 422 because of their flexibility, strength and severability. Of course, other means of attachment are contemplated, such as hooks, spring clamps, and the like. The holder 420 and valve 422 may be attached at relatively separated discrete points, as shown, or may be attached at multiple points along their mating surfaces to result in a more continuous coupling.

With reference to FIGS. 28, 29A, 29B and 33, an exemplary arrangement for joining each of the cusp supports 434 to the valve 422 with sutures is shown. Each cusp support 434 joins to the valve 422 with two lengths of suture material 480a, 480b that are secured to the handle connector 432 and extend in parallel segments down each of the legs 444. The lengths of suture material 480a, 480b couple to the handle connector 432 in a visible or otherwise accessible manner to enable severing by a knife blade. More specifically, and as seen in FIGS. 28 and 29A, the lengths of suture material 480a, 480b extending along each leg 444 are gathered at the lower end of the handle connector 432 and passed through an eye hole 475 provided in a flange 476 projecting outward from the distal hub member 473. The six strands of sutures then tie to a through hole 477 or other such feature in the proximal stem 470. In this manner, common segments 478 of all six sutures 480 are exposed on the exterior of the handle connector 432 to facilitate severing, or in other words the sutures 480 are routed so as to cross a common cut point on the holder 420.

As seen in FIG. 29B, each length of suture material 480a, 480b travels down the respective leg 444 and passes through a portion of the sewing band 440 at a loop 481. From the loops 481, each length of suture material 480a, 480b turns radially inward and fastens by tying at knots 482, for example, to one of the pieces 450a, 450b of the valve contacting portion 430. Anti-migration sleeves 483 (such as shrink-fit sleeves) prevent the knots 482 from sliding along the pieces 450a, 450b. As mentioned above, the suture may also be secured to a different part of the valve 422 than the sewing band 440, as long as it may easily be removed by pulling on its loose ends. The loop 481 is so formed and the sewing band 440 is constructed to permit the suture to slide from within the band by pulling one loose end.

FIG. 29D shows the cross-section through one of the exemplary holder legs 444, and in particular the two lengths of suture material 480a, 480b within a shaped sleeve 484 that conforms around the two juxtaposed leg halves 454a, 454b. The sleeve 484 may be formed of a polymer tube that is shrink fit around the two leg halves 454a, 454b. A cylindrical forming mandrel (not shown) is desirably placed in a triangular array along with the juxtaposed leg halves 454a, 454b, with the sleeve 484 circumscribing all three rods. After shrinking, the sleeve 484 conforms closely around the three rods and the mandrel is then removed, leaving the hollow space as shown for easy assembly and sliding passage of the two lengths of suture material 480a, 480b.

Figure 33:
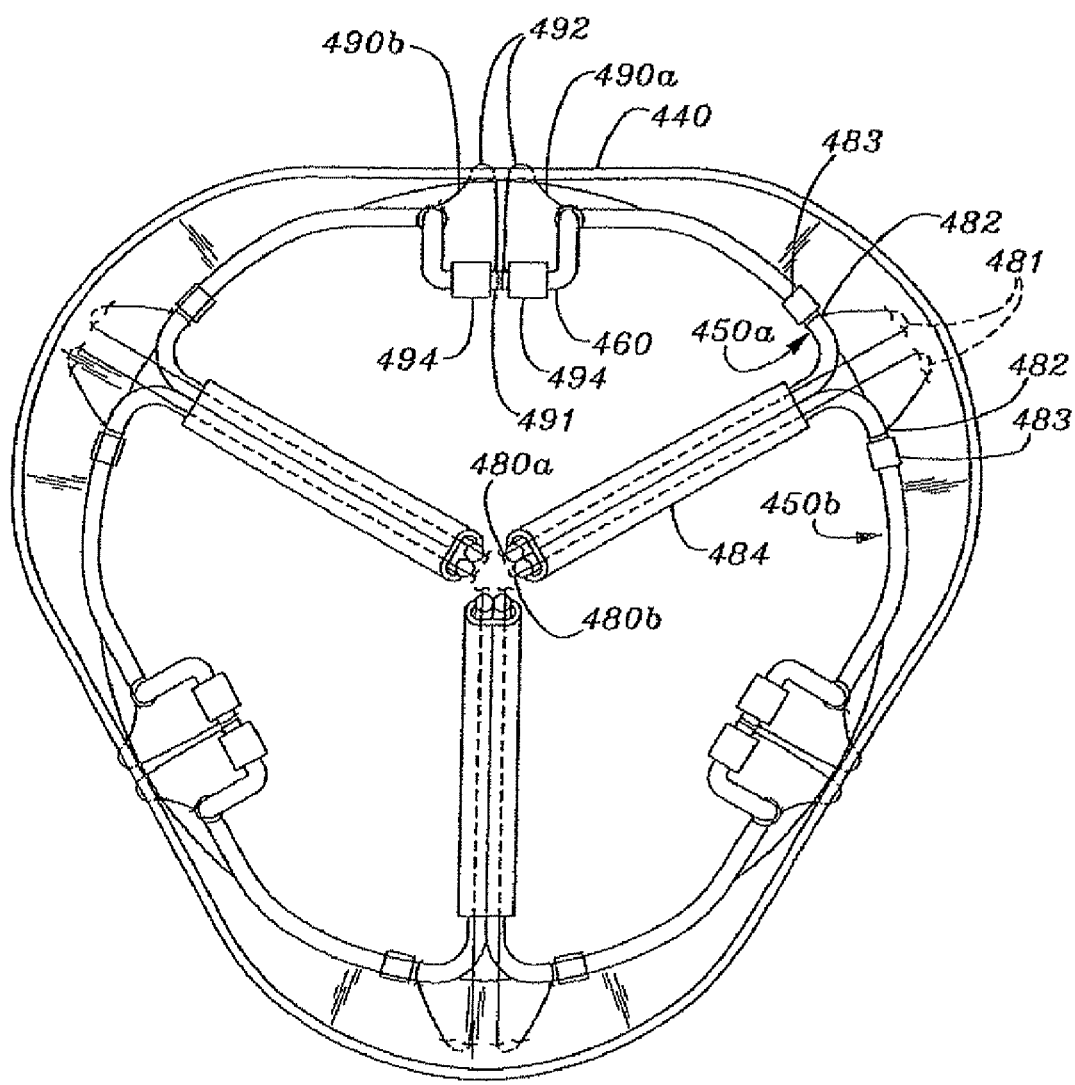
FIG. 33 is a top plan view of a portion of the valve holder of FIG. 28 attached to a flexible heart valve.

Now with reference to FIGS. 28, 29C and 33, two lengths of suture material 490a, 490b each extends from a first anchor or knot 491 secured to a midpoint of the leaflet guard section 460, via a loop 492 that passes through the sewing band 440, to a second anchor or knot 493 also on the leaflet guard section. In the embodiment shown, wherein the leaflet guard section 460 is part of a wire-like member, small anti-migration sleeves 494, 495 may be provided to prevent each knot 491, 493 from sliding along the wire. The segment of the sutures 490a, 490b that extend between the first knots 491 to the loop 492 are accessible for severing with a blade. The distance between the leaflet guard section 460 and sewing band 440 is exaggerated in the drawing, and the guard section will be desirably be configured to prevent the possibility of nicking the valve or leaflets with the blade.

In use, the holder 420 and valve 422 are removed from their sterile packaging in the operating room, and the valve washed or otherwise prepared for implant. The surgeon may wish to connect a longer handle to the holder using the handle coupling 472 of the connector 432. A typical handle length is between about 6-10 inches. After opening an access passage to the aortic valve implant site, the valve 422 is delivered using the holder 420 and attached handle.

There are two generally accepted methods for implanting a heart valve. In the first, called the interrupted or parachute suture method, a number of separate lengths of suture material are pre-anchored in the appropriate places in the native annulus and surrounding tissue. Each length loops through the tissue, and thus two free ends extend out of the implant site. The two free ends are then threaded through corresponding points on the sewing band 440. After all such sutures are pre-threaded through the native tissue and sewing band 440, the valve 422 is lowered along the array of sutures into position in the annulus. Each pair of free ends of the sutures is tied off to secure the valve in place with a plurality of separate one loop suture segments. The second method, called the running suture method, employs one or more sutures that extend in a series of loops through the native tissue and sewing band 440 for a more continuous structure. The surgeon threads the continuous suture through the annulus and valve after delivering the valve. In this method, visibility of the annulus and surrounding tissue may be occluded by the valve or holder, and so some manipulation of the valve and holder structure may be necessary.

Specifically, in the running suture method, the surgeon may manipulate the valve commissures 426 by flexing them inward along with the holder commissure supports 436 so as to visualize the implant site under the valve. Also, the longer handle may be removed from the connector 432 for greater visibility. As mentioned above, the preferred holder 420 is radially flexible to permit inward flexure and visualization of the implant site, but desirably resists deformation in either the axial or circumferential directions. Stiffness in the axial direction helps prevent excess compression of the valve 422 against the annulus caused by inadvertent excess axial force imparted by the surgeon. Resistance to torsional forces helps maintain the 120° orientation of the commissures 426. An added benefit of the radial flexibility of the holder 420 is its ability to be radially compressed to pass through delivery tubes smaller than the relaxed size of the holder/valve combination.

After attaching the valve to the annulus and ascending aorta using an interrupted pattern, or one or more continuous stitches, or other such means, the holder 420 is removed. To remove the holder 420, each suture at the commissures and cusps is severed. For the cusps, the common segments 478 of the lengths of suture material 480 (FIG. 29A) extending along each leg 444 are severed with one cut. At the commissures, the segments of suture that extend between the knots 491 and the loop 492 are severed, two at a time per commissure for a total of three cuts. The inwardly bent leaflet guard section 460 prevents the knife blade from contacting the leaflets during this operation. Therefore, there are a total of four cuts to release the valve from the holder. Each length of suture remains attached to the holder, and only free or loose segments pass through the valve. After severing all sutures, the holder may be removed from the now implanted valve 422, with the loose segments of sutures easily pulling free from the valve sewing band 440.

Figure 34:
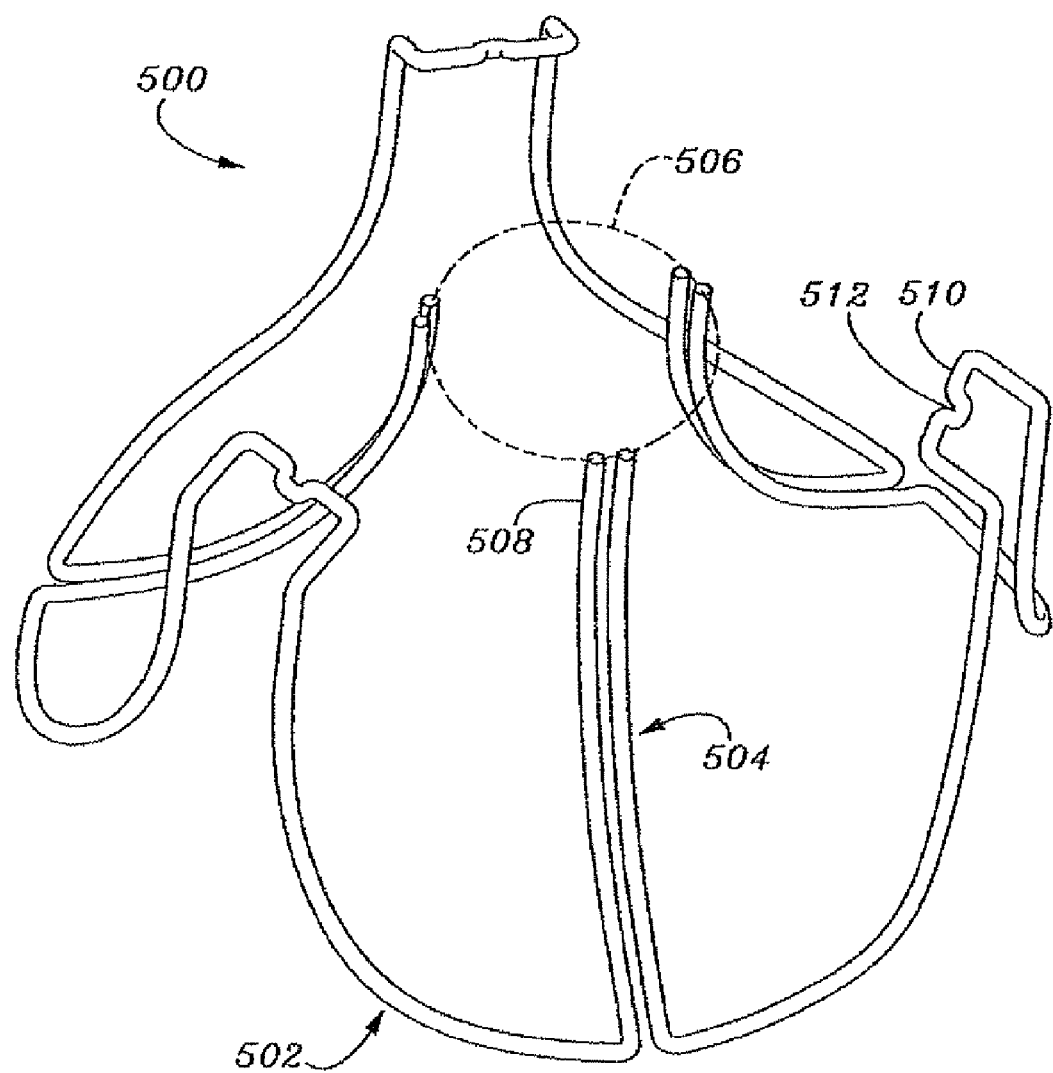
FIG. 34 is a perspective view of an alternative heart valve holder of the present invention having cusp and commissure supporting sections.

FIG. 34 illustrates a portion of an alternative valve holder 500 of the present invention similar to the holder 420 described above, and desirably comprising three sire-like pieces. Only a valve contacting portion 502 is shown, along with a plurality of legs 504 extending between cusp supports and a central location, defined by a circle 506 drawn in dashed line. Because of this modified arrangement, the inner ends 508 of the legs may be secured to the outside of a connecting member rather than the inside. Also, rather than anti-migration sleeves at the commissures, each leaflet guard section 510 includes a small anchor point 512, such as a section that is bent in a U-shape.

Figure 35:
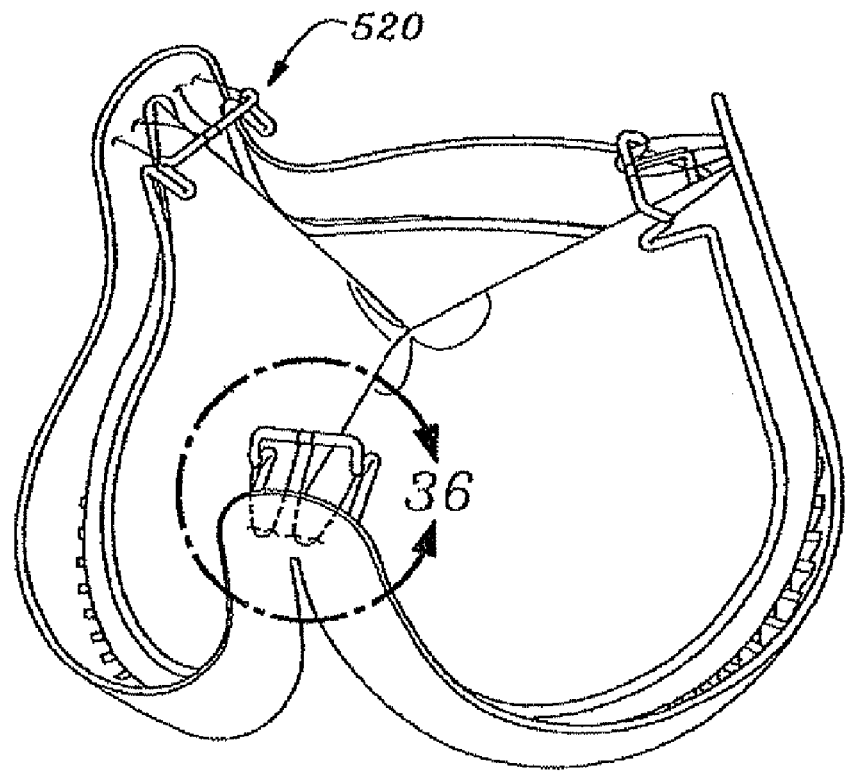
FIG. 35 is a perspective view of a still further alternative heart valve holder of the present invention having cusp and commissure supporting sections, and attachment points only at the valve commissures.
Figure 36:
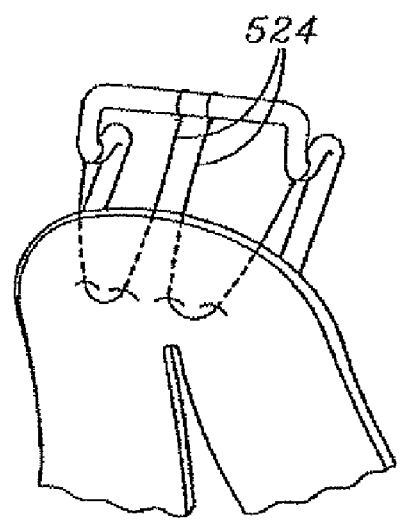
FIG. 36 is a detail view of a removable attachment of the holder of FIG. 35 to a valve commissure.

FIGS. 35 and 36 illustrate a still further holder 520 of the present invention having a single wire-like piece that conforms around the cusps and commissures of the valve 522. The holder 520 includes cusp and commissure supports but only attaches to the valve 522 at the three commissures, as indicated in the detail of FIG. 36. Specifically, one or more lengths of suture may be tied to bent portions of the commissure supports of the holder, with two shown having relatively more accessible severing segments 524 extending between the holder and valve. A separate handle or connecting member (not shown) may be used, or the holder may be removed using forceps.

Figure 37:
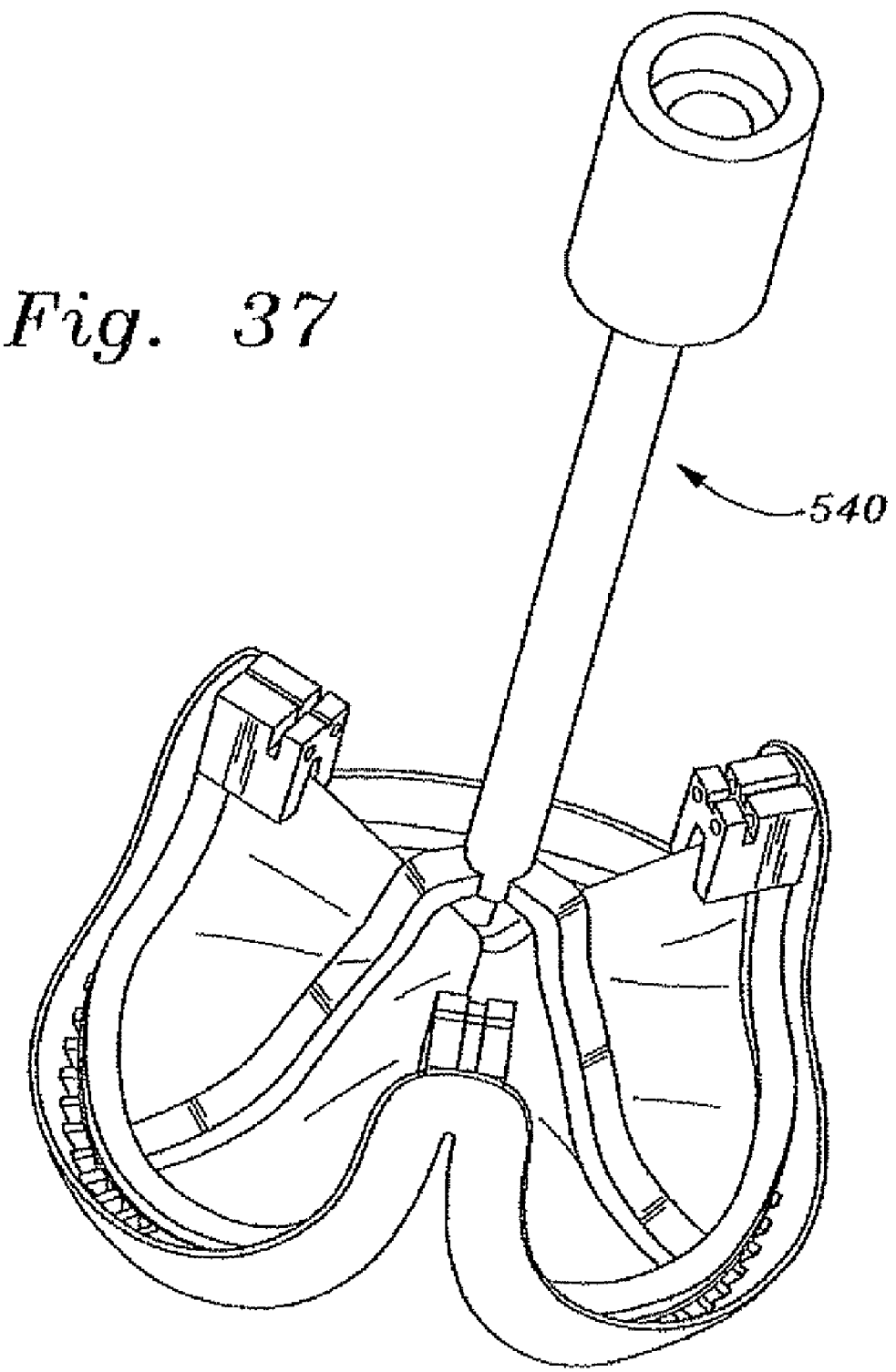
FIG. 37 is a perspective view of a one-piece heart valve holder of the present invention having cusp and commissure supporting sections.
Figure 38:
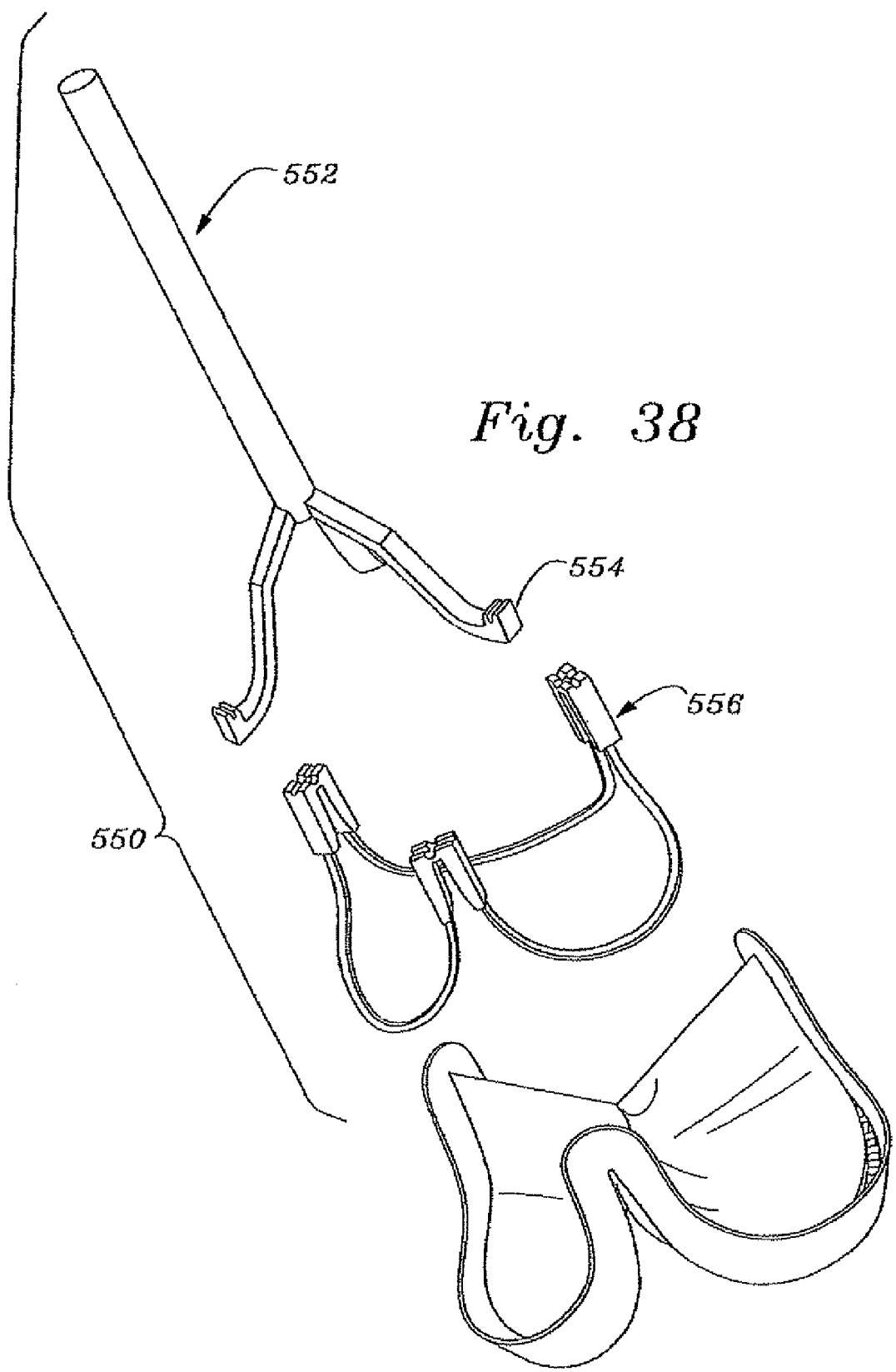
FIG. 38 is a perspective view of a two-piece heart valve holder of the present invention having cusp and commissure supporting sections.

FIGS. 37 and 38 illustrate a one-piece holder 540 and a two-piece holder 550, respectively. The holders 540, 550 may be molded pieces of Delrin or other suitable polymer. As before, both holders 540, 550 include cusp and commissure supports, and attach to a heart valve at three or six locations. The material is such that inward flexing of the cusp regions is permitted during the implant operation. In the two piece holder 550, a handle portion 552 along with radial legs 554 may be removed from a valve contacting portion 556 during implant for greater visibility of the implant area.

Figure 39:
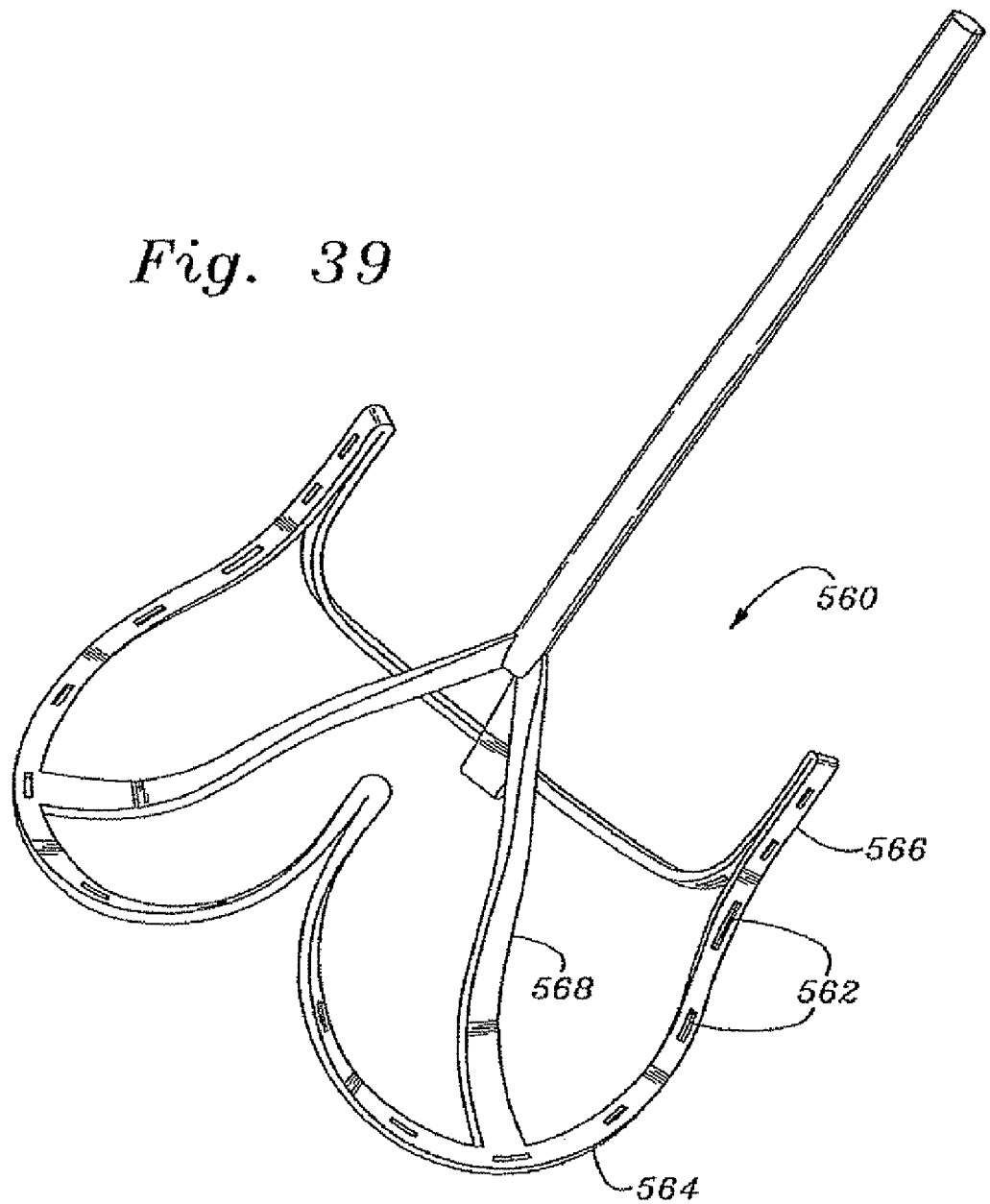
FIG. 39 is a perspective view of an alternative one-piece heart valve holder of the present invention having cusp and commissure supporting sections and a series of suture attachment apertures.

FIG. 39 illustrates a one-piece holder 560 that is similar to the one-piece holder 540 of FIG. 37 but includes a continuous series of suture apertures 562 along both the cusp supports 564 and commissure supports 566. Thus, the holder 560 may be relatively continuously coupled to a flexible heart valve to provide more uniform support thereto. It should also be noted that each leg 568 is molded so as to be relatively circumferentially wider close to the respective cusp support 564 than near the handle, and axially thicker near the handle than near the cusp support 564. This illustrates the potential for customizing the shape of the holders of the present invention (i.e., by molding) to provide either flexibility or rigidity in the appropriate places.

Figure 40:
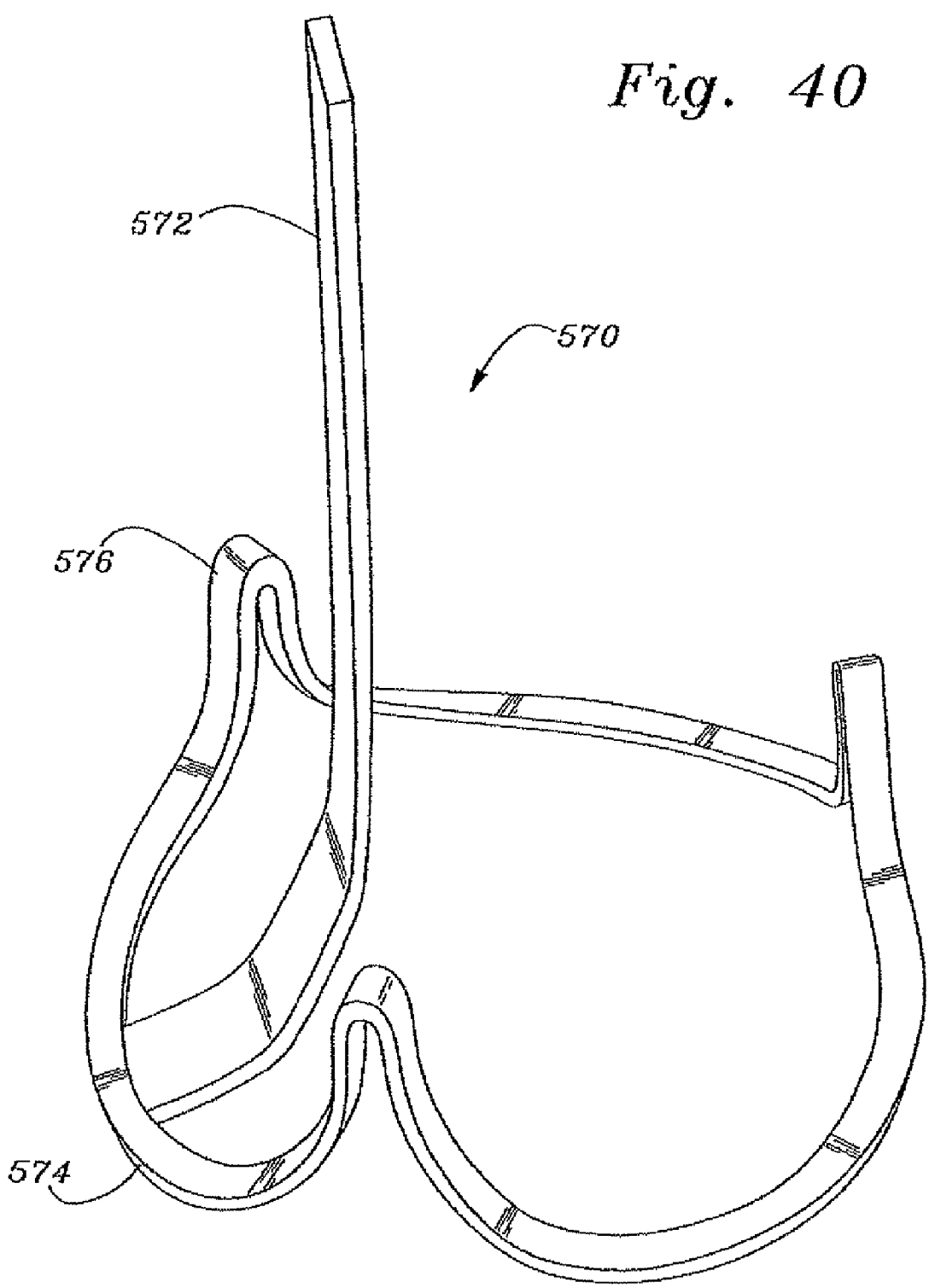
FIG. 40 is a perspective view of an alternative one-piece heart valve holder of the present invention having cusp and commissure supporting sections and a handle connection joined to a single cusp supporting section.

FIG. 40 shows a one-piece molded holder 570 that has a handle 572 that joins to a single cusp support 574. This arrangement minimizes structure within the periphery of the holder 570 and thus maximizes visibility of the valve attached thereto. Also, the three cusp supports 574 and three commissure supports 576 are decoupled and thus have greater flexibility in the radial direction than earlier embodiments where multiple legs from the holder periphery joined at a common point along the central axis.

Figure 41:
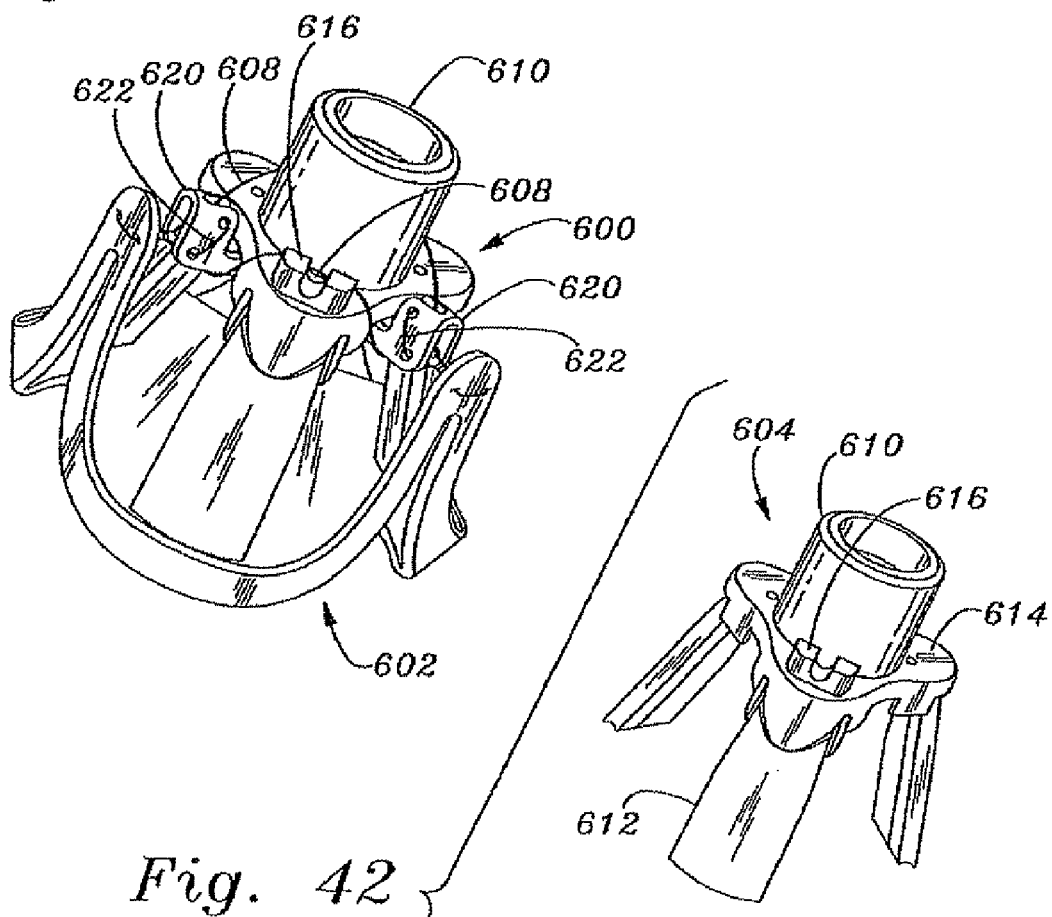
FIG. 41 is a perspective view of a two-stage heart valve holder of the present invention attached to a flexible heart valve.
Figure 42:
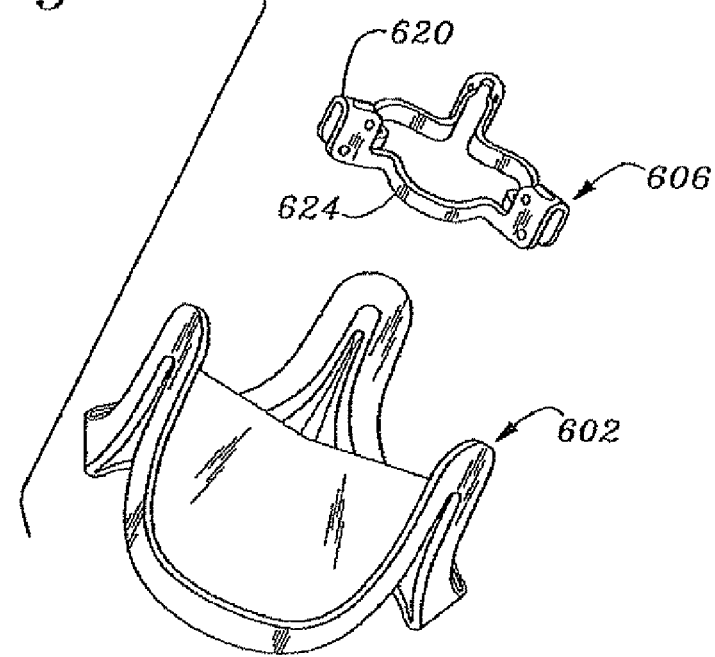
FIG. 42 is an exploded perspective view of the two-stage heart valve holder of FIG. 41.

FIGS. 41 and 42 are assembled and exploded views, respectively, of a two-stage holder 600 of the present invention, along with a flexible heart valve 602 such as described above. The holder 600 includes a relatively rigid stage 604 coupled to a relatively flexible stage 606 with one or more sutures 608. The rigid stage 604 forms a proximal part of the holder and includes a socket 610 for receiving a delivery handle (not shown). Three cusp supports 612 extend at an angle outward and distally from a base 614 on which the socket 610 resides. One or more cutting guides 616 may be provided on the base 614 over which the sutures 608 are threaded for easy release of the flexible stage 606 from the rigid stage 604. In the illustrated embodiment, a single suture 608 and single cutting guide 616 are used.

The flexible stage 606 includes three commissure supports 620 that include anchor holes or other such structure to which sutures 622 attach the supports to the commissures of the valve 602. The commissure supports 620 are coupled together with three relatively thin band segments 624 that permit relative radial flexing of the supports. Of course, other arrangements in which the commissure supports 620 are coupled together yet remain radially flexible with respect to one another are contemplated.

FIGS. 43 and 44 illustrate two modes of use of the holder 600 depending on the implant method. In the interrupted or parachute method, the relatively rigid stage 604 remains coupled to the relatively flexible stage 606 during delivery and anchoring of the valve 602. After implant, the sutures 622 holding the commissure supports 620 to the valve commissures are severed and the holder 600 pulled free. When the running suture method is used, the suture 608 is severed at the cutting guide 616 thus permitting the relatively rigid stage 604 to be removed, as seen in FIG. 44. The relatively flexible stage 606 remains attached to the valve 602 with the sutures 622. The arrows 626 illustrate the radial flexibility of the valve commissures as coupled to the relatively flexible stage 606, which flexibility is permitted by the three relatively thin band segments 624. Such flexibility helps the surgeon manipulate the holder/valve combination for greater visibility of the progress of the running sutures. At the same time, the circumferential orientation of the three valve commissures (and cusps) is maintained by the continued attachment of the flexible stage 606. After implant, the flexible stage 606 is removed by severing the sutures 622.

A holder for a highly flexible tissue-type heart valve is disclosed that maintains an implant shape to the valve. The holder may have cusp and commissure contacting supports, and may be attached at all six such supports, or only three. The holder may be flexible to permit inward flexing of the heart valve during implant for greater visibility when implanting using a running suture method. The holder may be formed of flexible wires such as Nitinol, and shaped to resist excessive axial and torsional deformation of the valve. A short handle connector suitable for manual grasping may be attached and stored with the valve, with the handle connector having a coupling for receiving a longer delivery handle. A two stage holder may be utilized to accommodate different implant methods.

The present invention may be embodied in other specific forms without departing from its spirit or essential characteristics. The described embodiments are to be considered in all respects only as illustrative and not restrictive. In particular, though the flexible nature of the present heart valve has been described as being particularly suitable for use in the aortic position, the advantage of flexibility could equally apply to a valve implanted in other positions, such as the mitral position. The scope of the invention is, therefore, indicated by the appended claims rather than by the foregoing description. All changes which come within the meaning and range of equivalency of the claims are to be embraced within their scope.

What is claimed is:

1. A suture-permeable connecting band formed of a silicone rubber inner member surrounded by a cloth cover, the connecting band having cusp portions separated by three upstanding commissure portions and attached to the stent/leaflet sub-assembly to provide outer free margins in the assembled heart valve and a flexible interface for suturing the valve to surrounding host tissue, wherein the connecting band closely conforms to the alternating stent cusps and commissures and defines an axial gap along the commissure portions opening to the inflow direction for enhancing freedom of movement of the stent cusps, the axial gap extending substantially the length of each commissure portion such that there is no structural connection between adjacent cusp portions except at an arcuate outflow tip of each commissure portion located approximately at the level of commissure tips of the flexible stent, wherein the outer free margins of the connecting band are angled upwardly and outwardly with respect to a central axis of the connecting band at each cusp portion and gradually re-align to be parallel to the central axis along the commissure portions.

2. The prosthetic heart valve of claim 1, wherein there are three stent cusps and three commissures.

3. The prosthetic heart valve of claim 1, wherein the cusp portions of the connecting band each define an inner generally radially oriented ledge for receiving and supporting the stent cusps.

4. The prosthetic heart valve of claim 1, wherein the stent comprises a fabric covered rod-like structure.

5. The prosthetic heart valve of claim 4, wherein the fabric covering closely surrounds the rod-like structure and exhibits a flap projecting outward therefrom substantially the entire length of the stent cusps and commissures to which leaflets attach.

6. The prosthetic heart valve of claim 5, wherein the flap has a width that varies along the cusps and commissures of the stent, the flap being narrower adjacent the stent cusps than adjacent the stent commissures.

7. The prosthetic heart valve of claim 5, wherein the leaflets each have an arcuate cusp edge and a coapting edge, and wherein the cusp edges of the leaflets attach between the connecting band and the fabric covering flap.

8. A highly flexible prosthetic heart valve, consisting essentially of:
  a flexible elongated stent formed generally in a tube with cusps on an inflow end alternating with commissure tips on an outflow end to form an undulating periphery, the stent having commissure regions on either side of each cusp wherein the commissure tips join adjacent commissure regions and the juxtaposed commissure regions define axial spaces therebetween that extend substantially the length of the adjacent commissure regions such that there is no structural connection between the adjacent commissure regions except at the respective commissure tip;
  a plurality of flexible leaflets attached to the stent so as to form a one-way valve within the stent, each leaflet defining a cusp margin; and
  a suture-permeable band attached and conforming to the undulating periphery of the stent and defining an axial gap opening to the inflow direction for enhancing freedom of movement of the stent cusps, the band supporting the stent on an inflow side of each cusp thereof and attaching to the outside of the stent at each commissure tip and providing suture-permeable interface between the assembled valve and surrounding host tissue, wherein the band includes arcuate cusp portions generally conforming to the stent cusps and commissure portions therebetween providing a suturing platform for connecting the heart valve to an anatomical orifice at each commissure tip, wherein the cusp margins of each leaflet are sandwiched between the stent cusps and the suture-permeable band.

9. The prosthetic heart valve of claim 8, wherein the commissure portions of the band each have an inverted U-shape.

10. The prosthetic heart valve of claim 8, wherein the commissure portions of the band are generally planar and axially aligned, and the cusp portions of the band each include an outwardly angled portion and an inwardly angled ledge sized to support the stent cusps.

11. The prosthetic heart valve of claim 10, wherein the inwardly angled ledges of the cusp portions of the band are sized to extend underneath the stent cusps.

12. The prosthetic heart valve of claim 10, wherein the suture-permeable band has a free margin for connecting the heart valve to an anatomical orifice including the outwardly angled portions at the cusp portions and generally axially-oriented margins at the commissure portions.

13. The prosthetic heart valve of claim 8, wherein the axial spaces of the stent are generally triangular and gradually increase in size from the attached commissure tips to the diverging cusps.

14. The prosthetic heart valve of claim 8, further comprising a fabric covering on the stent that exhibits a flap projecting outward therefrom substantially the entire length of the undulating periphery.

15. The prosthetic heart valve of claim 14, wherein the leaflets each have an arcuate cusp edge including the cusp margins and a coapting edge, and wherein the cusp edges of the leaflets attach between the suture-permeable band and the fabric covering flap.

16. A prosthetic heart valve, comprising:
  A flexible stent having alternating inflow cusps and outflow commissures, wherein the stent comprises a fabric covered rod-like structure, wherein the fabric covering closely surrounds the rod-like structure and exhibits a flap projecting outward therefrom substantially the entire length of the stent cusps and commissures;
  a plurality of flexible leaflets having cusp margins attached to the flap of the fabric covering the stent so as to form a stent/leaflet sub-assembly and a one-way valve within the stent; and
  a suture-permeable connecting band attached to the stent providing an interface between the valve and surrounding host tissue, wherein the leaflet cusp margins attach between the suture-permeable connecting band and the fabric flap of the stent, and wherein the connecting band conforms to the alternating stent cusps and commissures and has arcuate cusp portions alternating with U-shaped commissure portions, the connecting band defining an axial gap below the U-shaped commissure portions for enhancing freedom of movement of the stent cusps.

17. The prosthetic heart valve of claim 16, wherein the cusp portions each define an inner generally radially oriented ledge for receiving and supporting the stent cusps.

18. The prosthetic heart valve of claim 16, wherein the connecting band includes an outer free margin along a periphery thereof for connecting the heart valve to an anatomical orifice.

19. The prosthetic heart valve of claim 18, wherein the connecting band outer free margin angles upwardly and outwardly with respect to a central axis of the connecting band at each cusp portion and gradually re-aligns to be parallel to the central axis along the commissure portions.

20. The prosthetic heart valve of claim 16, wherein the leaflets each have an arcuate cusp edge and a coapting edge, and wherein the cusp edges of the leaflets attach between the connecting band and the fabric covering flap.

21. The connecting band of claim 16, wherein the fabric covering flap has a width that varies along the cusps and commissures of the stent, the flap being narrower adjacent the stent cusps than adjacent the stent commissures.

\* \* \* \* \*

UNITED STATES PATENT AND TRADEMARK OFFICE
CERTIFICATE OF CORRECTION

| | | |
|---|---|---|
| PATENT NO. | : 7,993,393 B2 | Page 1 of 1 |
| APPLICATION NO. | : 12/557404 | |
| DATED | : August 9, 2011 | |
| INVENTOR(S) | : Carpentier et al. | |

It is certified that error appears in the above-identified patent and that said Letters Patent is hereby corrected as shown below:

In the Claims:

Column 24, lines 61-62 cancel the text:

"1. A suture-permeable connecting band formed of a silicone rubber inner member surrounded by a cloth cover, the"

And replace it with the following portion of claim 1:

--1. A prosthetic heart valve, comprising:
  a stent/leaflet sub-assembly including a flexible stent having an undulating periphery with alternating inflow cusps and outflow commissures, and a plurality of flexible leaflets attached to the stent so as to form a one-way valve within the stent; and
  a suture-permeable connecting band formed of a silicone rubber inner member surrounded by a cloth cover, the--

Signed and Sealed this
Thirtieth Day of September, 2014

Michelle K. Lee
*Deputy Director of the United States Patent and Trademark Office*